United States Patent
McWhirter et al.

(10) Patent No.: US 10,952,416 B2
(45) Date of Patent: *Mar. 23, 2021

(54) METHOD FOR GENERATING A HUMANIZED TRANSGENIC MOUSE COMPRISING A HUMAN APRIL GENE

(71) Applicant: Regeneron Pharmaceuticals, Inc., Tarrytown, NY (US)

(72) Inventors: John McWhirter, Hastings-on-Hudson, NY (US); Cagan Gurer, Chappaqua, NY (US); Lynn Macdonald, Harrison, NY (US); Andrew J. Murphy, Croton-on-Hudson, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/001,070

(22) Filed: Jun. 6, 2018

(65) Prior Publication Data
US 2018/0271070 A1 Sep. 27, 2018

Related U.S. Application Data

(62) Division of application No. 14/537,320, filed on Nov. 10, 2014, now abandoned.

(60) Provisional application No. 61/905,986, filed on Nov. 19, 2013.

(51) Int. Cl.
| | |
|---|---|
| *A01K 67/027* | (2006.01) |
| *C07K 14/47* | (2006.01) |
| *C07K 14/705* | (2006.01) |
| *C12N 15/85* | (2006.01) |
| *G01N 33/50* | (2006.01) |

(52) U.S. Cl.
CPC .......... *A01K 67/0278* (2013.01); *C07K 14/47* (2013.01); *C07K 14/70575* (2013.01); *C12N 15/8509* (2013.01); *G01N 33/5005* (2013.01); *A01K 67/0271* (2013.01); *A01K 2207/12* (2013.01); *A01K 2207/15* (2013.01); *A01K 2217/052* (2013.01); *A01K 2217/07* (2013.01); *A01K 2217/072* (2013.01); *A01K 2227/105* (2013.01); *A01K 2267/03* (2013.01); *A01K 2267/0387* (2013.01); *C07K 2319/00* (2013.01); *C12N 2015/8527* (2013.01)

(58) Field of Classification Search
None
See application file for complete search history.

(56) References Cited

U.S. PATENT DOCUMENTS

2015/0143559 A1  5/2015  McWhirter et al.

FOREIGN PATENT DOCUMENTS

| CN | 1399556 A | 2/2003 |
|---|---|---|
| WO | 2006/128163 A2 | 11/2006 |
| WO | 2012/112544 A2 | 8/2012 |
| WO | 2013/063556 A1 | 5/2013 |

OTHER PUBLICATIONS

Novak A.J. et al., "Expression of BCMA, TACI, and BAFF-R in Multiple Myeloma: a Mechanims for Growth and Survival", Blood 103(2):689-694 (Jan. 15, 2004).
Japanese Notice of Reasons for Rejection dated Jul. 23, 2018 received in Japanese Patent Application No. 2016-527418, together with an English-language translation.
Bossen C. et al., "TACI, Unlike BAFF-R, is Solely Activated by Oligomeric BAFF and APRIL to Support Survival of Activated B Cells and Plasmablasts", Blood 111:1004-1012 (Feb. 2008).
Bossen C. et al., "BAFF, APRIL and Their Receptors: Structure, Function and Signaling", Seminars in Immunology 18:263-275 (2006).
Buehr M. et al., "Capture of Authentic Embryonic Stem Cells from Rat Blastocysts", Cell 135:1287-1298 (Dec. 26, 2008).
Castigli E. et al., "Impaired IgA Class Switching in APRIL-Deficient Mice", PNAS 101(11): 3903-3908 (Mar. 16, 2004).
Fernandez L. et al., "The TNF Family Member APRIL Dampens Collagen-Induced Arthritis", Ann Rheum Dis 72:1367-1374 (2013).
Guadagnoli M. et al., "Development and Characterization of APRIL Antagonistic Monoclonal Antibodies for Treatment of B-Cell Lymphomas", Blood 117(25):6856-6865 (2011).
Hahne M. et al., "APRIL, a New Ligand of the Tumor Necrosis Factor Family, Stimulates Tumor Cell Growth", J. Exp. Med. 188(6):1185-1190 (Sep. 1998).
Hardenberg G. et al., "APRIL Facilitates Viral-Induced Erythroleukemia But is Dispensable for T Cell Immunity and Lymphomagenesis", Journal of Leukocyte Biology 84:380-388 (Aug. 2006).
Hong J. et al, "Derivation and Characterization of Embryonic Stem Cells Lines Derived from Transgenic Fischer 344 and Dark Agouti Rats", Stem Cells and Development 21(9):1571-1586 (2010).
Kostenuik P.J. et al., "Denosumab, a Fully Human Monoclonal Antibody to RANKL, Inhibits Bone Resorption and Increases BMD in Knock-In Mice that Express Chimeric (Murine/Human) RANKL", Journal of Bone and Mineral Research 24:182-195 (Nov. 2, 2009).

(Continued)

*Primary Examiner* — Anoop K Singh
*Assistant Examiner* — Magdalene K Sgagias
(74) *Attorney, Agent, or Firm* — Scully, Scott, Murphy & Presser, P.C.; Elysa Goldberg

(57) ABSTRACT

Non-human animals, cells, methods and compositions for making and using the same are provided, wherein the non-human animals and cells comprise a humanized a proliferation-inducing ligand gene. Non-human animals and cells that express a human or humanized a proliferation-inducing ligand protein from an endogenous a proliferation-inducing ligand locus are described.

3 Claims, 6 Drawing Sheets

Specification includes a Sequence Listing.

(56) References Cited

OTHER PUBLICATIONS

Kruglov A.A. et al., "Modalities of Experimental TNF Blockade In Vivo: Mouse Models", Advances in TNF Family Research, Advances in Experimental Medicine and Biology 691:421-431 (Oct. 22, 2010).

Lascano V. et al., "The TNF Family Member APRIL Promotes Colorectal Tumorigenesis", Cell Death and Differentiation 19:1826-1835 (2012).

Li P. et al., "Germline Competent Embryonic Stem Cells Derived from Rat Blastocysts", Cell 135:1299-1310 (Dec. 26, 2008).

Mackay F. et al., "BAFF and APRIL: A Tutorial on B Cell Survival", Annu. Rev. Immunol. 21:231-264 (2003).

Planelles L. et al., "April Promotes B-1 Cell-Associated Neoplasm", Cancer Cell 6:399-408 (Oct. 2004).

Pradet-Balade B. et al., "An Endogenous Hybrid mRNA Encodes TWE-PRIL, a Functional Cell Surface TWEAK-APRIL Fusion Protein", The EMBO Journal 21(21):5711-5720 (2002).

Shultz L.D. et al., "Humanized Mice for Immune System Investigation: Progress, Promise and Challenges", Nature Reviews Immunology 12:786-798 (Nov. 2012).

Stein J.V. et al., "APRIL Modulates B and T Cell Immunity", J. Clin. Invest. 109:1587-1598 (2002).

Tong C. et al., "Production of p53 Gene Knockout Rats by Homologous Recombination in Embryonic Stem Cells", Nature 467:211-213 (Sep. 2010).

Willinger T. et al., "Improving Human Hemato-Lymphoid-System Mice by Cytokine Knock-in Gene Replacement", Trends in Immunology 32(7):321-327 (Jul. 2011).

Wolf A.I. et al., "Protective Antiviral Antibody Responses in a Mouse Model of Influenza Virus Infection Require TACI", The Journal of Clinical Investigation 121(10):3954-3964 (Oct. 2011).

Xiao Y. et al., "TNF Superfamily Member 13, APRIL, Inhibits Allergic Lung Inflammation", Eur J. Immunol. 41 (1):164-171 (Jan. 2011).

Xiao Y. et al., "APRIL (TNFSF13) Regulates Collagen Induced Arthritis, IL-17 Production and TH2 Response", Eur J. Immunol. 38(12):3450-3458 (Dec. 2008).

Yaccoby S. et al., "Atacicept (TACI-Ig) Inhibits Growth of TACIhigh Primary Myeloma Cells in SCID-hu Mice and in Coculture With Osteoclasts", Leukemia 22(2):406-413 (Feb. 2008).

"APRIL, Progress of a Proliferation-Inducing Ligand", China Biotechnology, pp. 7-11 (2004), together with an English-language abstract.

Qian Z. et al., "Expression of APRIL and its Significance in the Experimental Autoimmune Myocarditis", Medical Journal of Wuhan University 29(2):193-197 (Mar. 2008), together with an English-language abstract.

International Search Report and Written Opinion dated May 15, 2015 received in International Application No. PCT/US2014/064810.

Chinese Office Action dated Feb. 14, 2018 received in Chinese Patent Application No. 201480063162.8, together with an English-language translation.

SEQUENCE LISTING

<160> NUMBER OF SEQ ID NOS: 26

<210> SEQ ID NO 1
<211> LENGTH: 1676
<212> TYPE: DNA
<213> ORGANISM: Mus musculus

<400> SEQUENCE: 1

```
gaaggctggc cgctccttct gggtgtcacg gctgccctgt ccttcctaga taatggcacc      60
aaattctcct gaggctaggg gggaaggagt gtcagagtgt cactagctcg accctgggga     120
caagggggac taatagtacc ctagcttgat ttcttcctat tctcaagttc cttttttattt    180
```

```
ctcccttgcg taacccgctc ttcccttctg tgcctttgcc tgtattccca ccctccctgc    240
tacctcttgg ccacctcact tctgagacca cagctgttgg cagggtccct agctcatgcc    300
agcctcatct ccaggccaca tgggggctc agtcagagag ccagccctt cggttgctct      360
ttggttgagt tgggggcag ttctgggggc tgtgacttgt gctgtcgcac tactgatcca    420
acagacagag ctgcaaagcc taaggcggga ggtgagccgg ctgcagcgga gtggagggcc    480
ttcccagaag cagggagagc gcccatggca gagcctctgg gagcagagtc ctgatgtcct    540
ggaagcctgg aaggatgggg cgaaatctcg gagaaggaga gcagtactca cccagaagca    600
caagaagaag cactcagtcc tgcatcttgt tccagttaac attacctcca aggactctga    660
cgtgacagag gtgatgtggc aaccagtact taggcgtggg agaggcctgg aggcccaggg    720
agacattgta cgagtctggg acactggaat ttatctgctc tatagtcagg tcctgtttca    780
tgatgtgact ttcacaatgg gtcaggtggt atctcgggaa ggacaaggga aagagaaac    840
tctattccga tgtatcagaa gtatgccttc tgatcctgac cgtgcctaca atagctgcta    900
cagtgcaggt gtctttcatt tacatcaagg ggatattatc actgtcaaaa ttccacgggc    960
aaacgcaaaa cttagccttt ctccgcatgg aacattcctg gggtttgtga actatgatt    1020
gttataaagg gggtggggat ttcccattcc aaaaactggc tagacaaagg acaaggaacg    1080
gtcaagaaca gctctccatg gctttgcctt gactgttgtt cctccctttg cctttcccgc    1140
tcccactatc tgggctttga ctccatggat attaaaaaag tagaatattt tgtgtttatc    1200
tcccacacag ccccaaattc tttttgttgtg tgtgcgaagg gggttttgcg cactgtgcca    1260
agccttgtcc actggaatgc atccagaaca gcagcaccat ctagcggcag gttgaggaaa    1320
gactatggtc tctgctaggg aaaaccttat ccaactcttc aagtaccctc tgcttcaatt    1380
aacaagaagc ccggctttca gtatttcacc tattgcgtcc aaattcttgt tactatctag    1440
aaaaagatat atgttaggtg cctcgatatg catgccattc atcctcccca ttctcctata    1500
cacttccgag ctgggcactg agctttacgc cttaaatcac agtactcggg aggcagatct    1560
cgatgagttc gaggccaact tggtctaaat agtgagttcc aggccaccca ggggttacaa    1620
tggtgagacc ctgtctcaaa caaactaaca aacaaataaa cgaaaggctc tccacg        1676
```

<210> SEQ ID NO 2
<211> LENGTH: 240
<212> TYPE: PRT
<213> ORGANISM: Mus musculus

<400> SEQUENCE: 2

Met Pro Ala Ser Ser Pro Gly His Met Gly Gly Ser Val Arg Glu Pro
1               5                   10                  15

Ala Leu Ser Val Ala Leu Trp Leu Ser Trp Gly Ala Val Leu Gly Ala
            20                  25                  30

Val Thr Cys Ala Val Ala Leu Leu Ile Gln Gln Thr Glu Leu Gln Ser
        35                  40                  45

Leu Arg Arg Glu Val Ser Arg Leu Gln Arg Ser Gly Gly Pro Ser Gln
    50                  55                  60

Lys Gln Gly Glu Arg Pro Trp Gln Ser Leu Trp Glu Gln Ser Pro Asp
65                  70                  75                  80

Val Leu Glu Ala Trp Lys Asp Gly Ala Lys Ser Arg Arg Arg Arg Ala
                85                  90                  95

Val Leu Thr Gln Lys His Lys Lys Lys His Ser Val Leu His Leu Val
            100                 105                 110

```
Pro Val Asn Ile Thr Ser Lys Asp Ser Asp Val Thr Glu Val Met Trp
        115                 120                 125

Gln Pro Val Leu Arg Arg Gly Arg Gly Leu Glu Ala Gln Gly Asp Ile
130                 135                 140

Val Arg Val Trp Asp Thr Gly Ile Tyr Leu Leu Tyr Ser Gln Val Leu
145                 150                 155                 160

Phe His Asp Val Thr Phe Thr Met Gly Gln Val Val Ser Arg Glu Gly
                165                 170                 175

Gln Gly Arg Arg Glu Thr Leu Phe Arg Cys Ile Arg Ser Met Pro Ser
            180                 185                 190

Asp Pro Asp Arg Ala Tyr Asn Ser Cys Tyr Ser Ala Gly Val Phe His
        195                 200                 205

Leu His Gln Gly Asp Ile Ile Thr Val Lys Ile Pro Arg Ala Asn Ala
    210                 215                 220

Lys Leu Ser Leu Ser Pro His Gly Thr Phe Leu Gly Phe Val Lys Leu
225                 230                 235                 240

<210> SEQ ID NO 3
<211> LENGTH: 408
<212> TYPE: PRT
<213> ORGANISM: Mus musculus

<400> SEQUENCE: 3

Met Ala Ala Arg Arg Ser Gln Arg Arg Arg Gly Arg Gly Glu Pro
1               5                   10                  15

Gly Thr Ala Leu Leu Ala Pro Leu Val Leu Ser Leu Gly Leu Ala Leu
            20                  25                  30

Ala Cys Leu Gly Leu Leu Leu Val Val Ser Leu Gly Ser Trp Ala
        35                  40                  45

Thr Leu Ser Ala Gln Glu Pro Ser Gln Glu Glu Leu Thr Ala Glu Asp
50                  55                  60

Arg Arg Glu Pro Pro Glu Leu Asn Pro Gln Thr Glu Glu Ser Gln Asp
65                  70                  75                  80

Val Val Pro Phe Leu Glu Gln Leu Val Arg Pro Arg Arg Ser Ala Pro
                85                  90                  95

Lys Gly Arg Lys Ala Arg Pro Arg Ala Ile Ala Ala His Tyr Glu
            100                 105                 110

Val His Pro Arg Pro Gly Gln Asp Gly Ala Gln Ala Gly Val Asp Gly
        115                 120                 125

Thr Val Ser Gly Trp Glu Glu Thr Lys Ile Asn Ser Ser Ser Pro Leu
130                 135                 140

Arg Tyr Asp Arg Gln Ile Gly Glu Phe Thr Val Ile Arg Ala Gly Leu
145                 150                 155                 160

Tyr Tyr Leu Tyr Cys Gln Val His Phe Asp Glu Gly Lys Ala Val Tyr
                165                 170                 175

Leu Lys Leu Asp Leu Leu Val Asn Gly Val Leu Ala Leu Arg Cys Leu
            180                 185                 190

Glu Glu Phe Ser Ala Thr Ala Ala Ser Ser Pro Gly Pro Gln Leu Arg
        195                 200                 205

Leu Cys Gln Thr Glu Leu Gln Ser Leu Arg Arg Glu Val Ser Arg Leu
    210                 215                 220

Gln Arg Ser Gly Gly Pro Ser Gln Lys Gln Gly Glu Arg Pro Trp Gln
225                 230                 235                 240

Ser Leu Trp Glu Gln Ser Pro Asp Val Leu Glu Ala Trp Lys Asp Gly
```

```
                    245                 250                 255
Ala Lys Ser Arg Arg Arg Ala Val Leu Thr Gln Lys His Lys Lys
                260                 265                 270

Lys His Ser Val Leu His Leu Val Pro Val Asn Ile Thr Ser Lys Asp
            275                 280                 285

Ser Asp Val Thr Glu Val Met Trp Gln Pro Val Leu Arg Arg Gly Arg
        290                 295                 300

Gly Leu Glu Ala Gln Gly Asp Ile Val Arg Val Trp Asp Thr Gly Ile
305                 310                 315                 320

Tyr Leu Leu Tyr Ser Gln Val Leu Phe His Asp Val Thr Phe Thr Met
                325                 330                 335

Gly Gln Val Val Ser Arg Glu Gly Gln Gly Arg Arg Glu Thr Leu Phe
            340                 345                 350

Arg Cys Ile Arg Ser Met Pro Ser Asp Pro Asp Arg Ala Tyr Asn Ser
        355                 360                 365

Cys Tyr Ser Ala Gly Val Phe His Leu His Gln Gly Asp Ile Ile Thr
    370                 375                 380

Val Lys Ile Pro Arg Ala Asn Ala Lys Leu Ser Leu Ser Pro His Gly
385                 390                 395                 400

Thr Phe Leu Gly Phe Val Lys Leu
                405
```

<210> SEQ ID NO 4
<211> LENGTH: 2293
<212> TYPE: DNA
<213> ORGANISM: Homo sapiens

<400> SEQUENCE: 4

```
ccggaaccct gtgtgctggg gaggaatccc gcagtggccg gggggcttga ggccgctgct      60
ttgtctcttc gtccagagcc ttatgtaaga gcttttctcg ggaaacagga agtcctgctt     120
gccaatttca gcacagggag tagtgcaggc cttattccaa cacacccggc ccagccttaa     180
ccccagaact cagccagttt cttgcttccg tgccctggt tctcctcccc atcgagccca      240
cccctccttt cccaccttca gtcacccta gtgaactgcc ccagcgatct ctgctgtgct      300
tgaccccgag ggtcttccac cctcgccctg accctggaca ctgcccagct ggccccccca     360
tcctgctcct ggcacaatgc cctctagcca gccaacttc cctcccccaa ccctggggcc      420
gccccagggt tcctgcgcac tgcctgttcc tctgggtgt cactggcagc cctgtccttc      480
ctagagggac tggaacctaa ttctcctgag gctagggag ggtggagggt ctcaaggcaa      540
cgctggcccc acgacggagt gccaggagca ctaacagtac ccttagcttg ctttcctcct     600
ccctcctttt tattttcaag ttccttttta tttctccttg cgtaacaacc ttcttccctt     660
ctgcaccact gcccgtaccc ttacccgccc cgccacctcc ttgctacccc actcttgaaa     720
ccacagctgt tggcagggtc cccagctcat gccagcctca tctccttttct tgctagcccc    780
caaagggcct ccaggcaaca tggggggccc agtcagagag ccggcactct cagttgcccc    840
ctggttgagt tgggggggcag ctctgggggc cgtggcttgt gccatggctc tgctgaccca    900
acaaacagag ctgcagagcc tcaggagaga ggtgagccgg ctgcagggga caggaggccc    960
ctcccagaat ggggaagggt atccctggca gagtctcccg gagcagagtt ccgatgccct   1020
ggaagcctgg gagaatgggg agagatcccg gaaaaggaga gcagtgctca cccaaaaaca   1080
gaagaagcag cactctgtcc tgcacctggt tcccattaac gccacctcca aggatgactc   1140
cgatgtgaca gaggtgatgt ggcaaccagc tcttaggcgt gggagaggcc tacaggccca   1200
```

```
aggatatggt gtccgaatcc aggatgctgg agtttatctg ctgtatagcc aggtcctgtt    1260
tcaagacgtg actttcacca tgggtcaggt ggtgtctcga gaaggccaag gaaggcagga    1320
gactctattc cgatgtataa gaagtatgcc ctcccacccg gaccgggcct acaacagctg    1380
ctatagcgca ggtgtcttcc atttacacca aggggatatt ctgagtgtca taattccccg    1440
ggcaagggcg aaacttaacc tctctccaca tggaaccttc ctggggtttg tgaaactgtg    1500
attgtgttat aaaaagtggc tcccagcttg aagaccagg gtgggtacat actggagaca    1560
gccaagagct gagtatataa aggagaggga atgtgcagga acagaggcgt cttcctgggt    1620
ttggctcccc gttcctcact tttccctttt cattcccacc ccctagactt tgattttacg    1680
gatatcttgc ttctgttccc catggagctc cgaattcttg cgtgtgtgta gatgaggggc    1740
gggggacggg cgccaggcat tgtccagacc tggtcgggc ccactggaag catccagaac    1800
agcaccacca tctagcggcc gctcgaggga agcacccgcc ggttggccga agtccacgaa    1860
gccgccctct gctagggaaa acccctggtt ctccatgcca cacctctctc caggtgccct    1920
ctgcctcttc accccacaag aagccttatc ctacgtcctt ctctccatct atcggacccc    1980
agtttccatc actatctcca gagatgtagc tattatgcgc ccgtctacag ggggtgcccg    2040
acgatgacgg tgccttcgca gtcaaattac tcttcgggtc ccaaggtttg gctttcacgc    2100
gctccattgc cccggcgtgg caggccattc aagcccttc cgggctggaa ctggtgtcgg    2160
aggagcctcg ggtgtatcgt acgccctggt gttggtgttg cctcactcct ctgagctctt    2220
ctttctgatc aagccctgct taaagttaaa taaaatagaa tgaatgatac cccggcaaaa    2280
aaaaaaaaaa aaa                                                        2293

<210> SEQ ID NO 5
<211> LENGTH: 250
<212> TYPE: PRT
<213> ORGANISM: Homo sapiens

<400> SEQUENCE: 5

Met Pro Ala Ser Ser Pro Phe Leu Leu Ala Pro Lys Gly Pro Pro Gly
1               5                   10                  15

Asn Met Gly Gly Pro Val Arg Glu Pro Ala Leu Ser Val Ala Leu Trp
            20                  25                  30

Leu Ser Trp Gly Ala Ala Leu Gly Ala Val Ala Cys Ala Met Ala Leu
        35                  40                  45

Leu Thr Gln Gln Thr Glu Leu Gln Ser Leu Arg Arg Glu Val Ser Arg
    50                  55                  60

Leu Gln Gly Thr Gly Gly Pro Ser Gln Asn Gly Glu Gly Tyr Pro Trp
65                  70                  75                  80

Gln Ser Leu Pro Glu Gln Ser Ser Asp Ala Leu Glu Ala Trp Glu Asn
                85                  90                  95

Gly Glu Arg Ser Arg Lys Arg Arg Ala Val Leu Thr Gln Lys Gln Lys
            100                 105                 110

Lys Gln His Ser Val Leu His Leu Val Pro Ile Asn Ala Thr Ser Lys
        115                 120                 125

Asp Asp Ser Asp Val Thr Glu Val Met Trp Gln Pro Ala Leu Arg Arg
    130                 135                 140

Gly Arg Gly Leu Gln Ala Gln Gly Tyr Gly Val Arg Ile Gln Asp Ala
145                 150                 155                 160

Gly Val Tyr Leu Leu Tyr Ser Gln Val Leu Phe Gln Asp Val Thr Phe
                165                 170                 175
```

Thr Met Gly Gln Val Val Ser Arg Glu Gly Gln Gly Arg Gln Glu Thr
                180                 185                 190

Leu Phe Arg Cys Ile Arg Ser Met Pro Ser His Pro Asp Arg Ala Tyr
            195                 200                 205

Asn Ser Cys Tyr Ser Ala Gly Val Phe His Leu His Gln Gly Asp Ile
        210                 215                 220

Leu Ser Val Ile Ile Pro Arg Ala Arg Ala Lys Leu Asn Leu Ser Pro
225                 230                 235                 240

His Gly Thr Phe Leu Gly Phe Val Lys Leu
                245                 250

<210> SEQ ID NO 6
<211> LENGTH: 234
<212> TYPE: PRT
<213> ORGANISM: Homo sapiens

<400> SEQUENCE: 6

Met Pro Ala Ser Ser Pro Phe Leu Leu Ala Pro Lys Gly Pro Pro Gly
1               5                   10                  15

Asn Met Gly Gly Pro Val Arg Glu Pro Ala Leu Ser Val Ala Leu Trp
            20                  25                  30

Leu Ser Trp Gly Ala Ala Leu Gly Ala Val Ala Cys Ala Met Ala Leu
        35                  40                  45

Leu Thr Gln Gln Thr Glu Leu Gln Ser Leu Arg Arg Glu Val Ser Arg
    50                  55                  60

Leu Gln Gly Thr Gly Gly Pro Ser Gln Asn Gly Glu Gly Tyr Pro Trp
65                  70                  75                  80

Gln Ser Leu Pro Glu Gln Ser Ser Asp Ala Leu Glu Ala Trp Glu Asn
                85                  90                  95

Gly Glu Arg Ser Arg Lys Arg Arg Ala Val Leu Thr Gln Lys Gln Lys
            100                 105                 110

Asn Asp Ser Asp Val Thr Glu Val Met Trp Gln Pro Ala Leu Arg Arg
        115                 120                 125

Gly Arg Gly Leu Gln Ala Gln Gly Tyr Gly Val Arg Ile Gln Asp Ala
    130                 135                 140

Gly Val Tyr Leu Leu Tyr Ser Gln Val Leu Phe Gln Asp Val Thr Phe
145                 150                 155                 160

Thr Met Gly Gln Val Val Ser Arg Glu Gly Gln Gly Arg Gln Glu Thr
                165                 170                 175

Leu Phe Arg Cys Ile Arg Ser Met Pro Ser His Pro Asp Arg Ala Tyr
            180                 185                 190

Asn Ser Cys Tyr Ser Ala Gly Val Phe His Leu His Gln Gly Asp Ile
        195                 200                 205

Leu Ser Val Ile Ile Pro Arg Ala Arg Ala Lys Leu Asn Leu Ser Pro
    210                 215                 220

His Gly Thr Phe Leu Gly Phe Val Lys Leu
225                 230

<210> SEQ ID NO 7
<211> LENGTH: 247
<212> TYPE: PRT
<213> ORGANISM: Homo sapiens

<400> SEQUENCE: 7

Met Pro Ala Ser Ser Pro Phe Leu Leu Ala Pro Lys Gly Pro Pro Gly
1               5                   10                  15

Asn Met Gly Gly Pro Val Arg Glu Pro Ala Leu Ser Val Ala Leu Trp
            20                  25                  30

Leu Ser Trp Gly Ala Ala Leu Gly Ala Val Ala Cys Ala Met Ala Leu
        35                  40                  45

Leu Thr Gln Gln Thr Glu Leu Gln Ser Leu Arg Arg Glu Val Ser Arg
    50                  55                  60

Leu Gln Gly Thr Gly Gly Pro Ser Gln Asn Gly Glu Gly Tyr Pro Trp
65                  70                  75                  80

Gln Ser Leu Pro Glu Gln Ser Ser Asp Ala Leu Glu Ala Trp Glu Asn
                85                  90                  95

Gly Glu Arg Ser Arg Lys Arg Arg Ala Val Leu Thr Gln Lys Gln Lys
            100                 105                 110

Lys Gln His Ser Val Leu His Leu Val Pro Ile Asn Ala Thr Ser Lys
        115                 120                 125

Asp Asp Ser Asp Val Thr Glu Val Met Trp Gln Pro Ala Leu Arg Arg
    130                 135                 140

Gly Arg Gly Leu Gln Ala Gln Gly Tyr Gly Val Arg Ile Gln Asp Ala
145                 150                 155                 160

Gly Val Tyr Leu Leu Tyr Ser Gln Val Leu Phe Gln Asp Val Thr Phe
                165                 170                 175

Thr Met Gly Gln Val Val Ser Arg Glu Gly Gln Gly Arg Gln Glu Thr
            180                 185                 190

Leu Phe Arg Cys Ile Arg Ser Met Pro Ser His Pro Asp Arg Ala Tyr
        195                 200                 205

Asn Ser Cys Tyr Ser Ala Gly Val Phe His Leu His Gln Gly Asp Ile
    210                 215                 220

Leu Ser Val Ile Ile Pro Arg Ala Arg Ala Lys Leu Asn Leu Ser Pro
225                 230                 235                 240

His Gly Thr Phe Leu Gly Leu
                245

<210> SEQ ID NO 8
<211> LENGTH: 223
<212> TYPE: PRT
<213> ORGANISM: Homo sapiens

<400> SEQUENCE: 8

Met Pro Ala Ser Ser Pro Phe Leu Leu Ala Pro Lys Gly Pro Pro Gly
1               5                   10                  15

Asn Met Gly Gly Pro Val Arg Glu Pro Ala Leu Ser Val Ala Leu Trp
            20                  25                  30

Leu Ser Trp Gly Ala Ala Leu Gly Ala Val Ala Cys Ala Met Ala Leu
        35                  40                  45

Leu Thr Gln Gln Thr Glu Leu Gln Ser Leu Arg Arg Glu Val Ser Arg
    50                  55                  60

Leu Gln Gly Thr Gly Gly Pro Ser Gln Asn Gly Glu Gly Tyr Pro Trp
65                  70                  75                  80

Gln Ser Leu Pro Glu Gln Gln His Ser Val Leu His Leu Val Pro Ile
                85                  90                  95

Asn Ala Thr Ser Lys Asp Asp Ser Asp Val Thr Glu Val Met Trp Gln
            100                 105                 110

Pro Ala Leu Arg Arg Gly Arg Gly Leu Gln Ala Gln Gly Tyr Gly Val
        115                 120                 125

Arg Ile Gln Asp Ala Gly Val Tyr Leu Leu Tyr Ser Gln Val Leu Phe

```
                130                 135                 140
Gln Asp Val Thr Phe Thr Met Gly Gln Val Val Ser Arg Glu Gly Gln
145                 150                 155                 160

Gly Arg Gln Glu Thr Leu Phe Arg Cys Ile Arg Ser Met Pro Ser His
                165                 170                 175

Pro Asp Arg Ala Tyr Asn Ser Cys Tyr Ser Ala Gly Val Phe His Leu
                180                 185                 190

His Gln Gly Asp Ile Leu Ser Val Ile Ile Pro Arg Ala Arg Ala Lys
                195                 200                 205

Leu Asn Leu Ser Pro His Gly Thr Phe Leu Gly Phe Val Lys Leu
            210                 215                 220

<210> SEQ ID NO 9
<211> LENGTH: 222
<212> TYPE: PRT
<213> ORGANISM: Homo sapiens

<400> SEQUENCE: 9

Met Pro Ala Ser Ser Pro Phe Leu Leu Ala Pro Lys Gly Pro Pro Gly
1               5                   10                  15

Asn Met Gly Gly Pro Val Arg Glu Pro Ala Leu Ser Val Ala Leu Trp
                20                  25                  30

Leu Ser Trp Gly Ala Ala Leu Gly Ala Val Ala Cys Ala Met Ala Leu
            35                  40                  45

Leu Thr Gln Gln Thr Glu Leu Gln Ser Leu Arg Arg Glu Val Ser Arg
        50                  55                  60

Leu Gln Gly Thr Gly Gly Pro Ser Gln Asn Gly Glu Gly Tyr Pro Trp
65                  70                  75                  80

Gln Ser Leu Pro Glu Gln His Ser Val Leu His Leu Val Pro Ile Asn
                85                  90                  95

Ala Thr Ser Lys Asp Asp Ser Asp Val Thr Glu Val Met Trp Gln Pro
                100                 105                 110

Ala Leu Arg Arg Gly Arg Gly Leu Gln Ala Gln Gly Tyr Gly Val Arg
            115                 120                 125

Ile Gln Asp Ala Gly Val Tyr Leu Leu Tyr Ser Gln Val Leu Phe Gln
        130                 135                 140

Asp Val Thr Phe Thr Met Gly Gln Val Val Ser Arg Glu Gly Gln Gly
145                 150                 155                 160

Arg Gln Glu Thr Leu Phe Arg Cys Ile Arg Ser Met Pro Ser His Pro
                165                 170                 175

Asp Arg Ala Tyr Asn Ser Cys Tyr Ser Ala Gly Val Phe His Leu His
                180                 185                 190

Gln Gly Asp Ile Leu Ser Val Ile Ile Pro Arg Ala Arg Ala Lys Leu
            195                 200                 205

Asn Leu Ser Pro His Gly Thr Phe Leu Gly Phe Val Lys Leu
        210                 215                 220

<210> SEQ ID NO 10
<211> LENGTH: 205
<212> TYPE: PRT
<213> ORGANISM: Homo sapiens

<400> SEQUENCE: 10

Met Gly Gly Pro Val Arg Glu Pro Ala Leu Ser Val Ala Leu Trp Leu
1               5                   10                  15

Ser Trp Gly Ala Ala Leu Gly Ala Val Ala Cys Ala Met Ala Leu Leu
```

```
            20                  25                  30
Thr Gln Gln Thr Glu Leu Gln Ser Leu Arg Arg Glu Val Ser Arg Leu
             35                  40                  45

Gln Gly Thr Gly Gly Pro Ser Gln Asn Gly Glu Gly Tyr Pro Trp Gln
         50                  55                  60

Ser Leu Pro Glu Gln His Ser Val Leu His Leu Val Pro Ile Asn Ala
 65                  70                  75                  80

Thr Ser Lys Asp Asp Ser Asp Val Thr Glu Val Met Trp Gln Pro Ala
                 85                  90                  95

Leu Arg Arg Gly Arg Gly Leu Gln Ala Gln Gly Tyr Gly Val Arg Ile
            100                 105                 110

Gln Asp Ala Gly Val Tyr Leu Leu Tyr Ser Gln Val Leu Phe Gln Asp
        115                 120                 125

Val Thr Phe Thr Met Gly Gln Val Val Ser Arg Glu Gly Gln Gly Arg
    130                 135                 140

Gln Glu Thr Leu Phe Arg Cys Ile Arg Ser Met Pro Ser His Pro Asp
145                 150                 155                 160

Arg Ala Tyr Asn Ser Cys Tyr Ser Ala Gly Val Phe His Leu His Gln
                165                 170                 175

Gly Asp Ile Leu Ser Val Ile Ile Pro Arg Ala Arg Ala Lys Leu Asn
            180                 185                 190

Leu Ser Pro His Gly Thr Phe Leu Gly Phe Val Lys Leu
        195                 200                 205

<210> SEQ ID NO 11
<211> LENGTH: 330
<212> TYPE: PRT
<213> ORGANISM: Homo sapiens

<400> SEQUENCE: 11

Met Ala Ala Arg Arg Ser Gln Arg Arg Gly Arg Arg Gly Glu Pro
1               5                  10                  15

Gly Thr Ala Leu Leu Val Pro Leu Ala Leu Gly Leu Gly Leu Ala Leu
            20                  25                  30

Ala Cys Leu Gly Leu Leu Leu Ala Val Val Ser Leu Gly Ser Arg Ala
        35                  40                  45

Ser Leu Ser Ala Gln Glu Pro Ala Gln Glu Glu Leu Val Ala Glu Glu
    50                  55                  60

Asp Gln Asp Pro Ser Glu Leu Asn Pro Gln Thr Glu Glu Ser Gln Asp
 65                  70                  75                  80

Pro Ala Pro Phe Leu Asn Arg Leu Val Arg Pro Arg Arg Ser Ala Pro
                 85                  90                  95

Lys Gly Arg Lys Thr Arg Ala Arg Arg Ala Ile Ala Ala His Tyr Glu
            100                 105                 110

Val His Pro Arg Pro Gly Gln Asp Gly Ala Gln Ala Gly Val Asp Gly
        115                 120                 125

Thr Val Ser Gly Trp Glu Glu Ala Arg Ile Asn Ser Ser Ser Pro Leu
    130                 135                 140

Arg Tyr Asn Arg Gln Ile Gly Glu Phe Ile Val Thr Arg Ala Gly Leu
145                 150                 155                 160

Tyr Tyr Leu Tyr Cys Gln Ser Ser Asp Ala Leu Glu Ala Trp Glu Asn
                165                 170                 175

Gly Glu Arg Ser Arg Lys Arg Arg Ala Val Leu Thr Gln Lys Gln Lys
            180                 185                 190
```

Lys Gln His Ser Val Leu His Leu Val Pro Ile Asn Ala Thr Ser Lys
                195                 200                 205

Asp Asp Ser Asp Val Thr Glu Val Met Trp Gln Pro Ala Leu Arg Arg
210                 215                 220

Gly Arg Gly Leu Gln Ala Gln Gly Tyr Gly Val Arg Ile Gln Asp Ala
225                 230                 235                 240

Gly Val Tyr Leu Leu Tyr Ser Gln Val Leu Phe Gln Asp Val Thr Phe
                245                 250                 255

Thr Met Gly Gln Val Val Ser Arg Glu Gly Gln Gly Arg Gln Glu Thr
                260                 265                 270

Leu Phe Arg Cys Ile Arg Ser Met Pro Ser His Pro Asp Arg Ala Tyr
                275                 280                 285

Asn Ser Cys Tyr Ser Ala Gly Val Phe His Leu His Gln Gly Asp Ile
                290                 295                 300

Leu Ser Val Ile Ile Pro Arg Ala Arg Ala Lys Leu Asn Leu Ser Pro
305                 310                 315                 320

His Gly Thr Phe Leu Gly Phe Val Lys Leu
                325                 330

<210> SEQ ID NO 12
<211> LENGTH: 241
<212> TYPE: PRT
<213> ORGANISM: Artificial Sequence
<220> FEATURE:
<223> OTHER INFORMATION: Humanized APRIL Protein

<400> SEQUENCE: 12

Met Pro Ala Ser Ser Pro Gly His Met Gly Gly Ser Val Arg Glu Pro
1               5                   10                  15

Ala Leu Ser Val Ala Leu Trp Leu Ser Trp Gly Ala Val Leu Gly Ala
                20                  25                  30

Val Thr Cys Ala Val Ala Leu Leu Ile Gln Gln Thr Glu Leu Gln Ser
            35                  40                  45

Leu Arg Arg Glu Val Ser Arg Leu Gln Arg Ser Gly Gly Pro Ser Gln
    50                  55                  60

Lys Gln Gly Glu Arg Pro Trp Gln Ser Leu Trp Glu Gln Ser Ser Asp
65                  70                  75                  80

Ala Leu Glu Ala Trp Glu Asn Gly Glu Arg Ser Arg Lys Arg Arg Ala
                85                  90                  95

Val Leu Thr Gln Lys Gln Lys Lys Gln His Ser Val Leu His Leu Val
                100                 105                 110

Pro Ile Asn Ala Thr Ser Lys Asp Asp Ser Asp Val Thr Glu Val Met
            115                 120                 125

Trp Gln Pro Ala Leu Arg Arg Gly Arg Gly Leu Gln Ala Gln Gly Tyr
        130                 135                 140

Gly Val Arg Ile Gln Asp Ala Gly Val Tyr Leu Leu Tyr Ser Gln Val
145                 150                 155                 160

Leu Phe Gln Asp Val Thr Phe Thr Met Gly Gln Val Val Ser Arg Glu
                165                 170                 175

Gly Gln Gly Arg Gln Glu Thr Leu Phe Arg Cys Ile Arg Ser Met Pro
                180                 185                 190

Ser His Pro Asp Arg Ala Tyr Asn Ser Cys Tyr Ser Ala Gly Val Phe
            195                 200                 205

His Leu His Gln Gly Asp Ile Leu Ser Val Ile Ile Pro Arg Ala Arg
        210                 215                 220

```
Ala Lys Leu Asn Leu Ser Pro His Gly Thr Phe Leu Gly Phe Val Lys
225                 230                 235                 240

Leu

<210> SEQ ID NO 13
<211> LENGTH: 19
<212> TYPE: DNA
<213> ORGANISM: Artificial Sequence
<220> FEATURE:
<223> OTHER INFORMATION: Synthetic Oligonucleotide: mApril-1, mApril
      exon 4, Forward

<400> SEQUENCE: 13
gaggcccagg gagacattg                                              19

<210> SEQ ID NO 14
<211> LENGTH: 20
<212> TYPE: DNA
<213> ORGANISM: Artificial Sequence
<220> FEATURE:
<223> OTHER INFORMATION: Synthetic Oligonucleotide: mApril-1, mApril
      exon 4, Reverse

<400> SEQUENCE: 14
gcaggctcag ggcttatctg                                             20

<210> SEQ ID NO 15
<211> LENGTH: 28
<212> TYPE: DNA
<213> ORGANISM: Artificial Sequence
<220> FEATURE:
<223> OTHER INFORMATION: Synthetic Oligonucleotide: mApril-1, mApril
      exon 4, Probe

<400> SEQUENCE: 15
cgagtctggg acactggaat ttatctgc                                    28

<210> SEQ ID NO 16
<211> LENGTH: 22
<212> TYPE: DNA
<213> ORGANISM: Artificial Sequence
<220> FEATURE:
<223> OTHER INFORMATION: Synthetic Oligonucleotide: mApril-2, mApril
      intron 5, Forward

<400> SEQUENCE: 16
aacttgctcc atcccttaca tc                                          22

<210> SEQ ID NO 17
<211> LENGTH: 24
<212> TYPE: DNA
<213> ORGANISM: Artificial Sequence
<220> FEATURE:
<223> OTHER INFORMATION: Synthetic Oligonucleotide: mApril-2, mApril
      intron 5, Reverse

<400> SEQUENCE: 17
gcttgagagt tggttccttc cttt                                        24

<210> SEQ ID NO 18
<211> LENGTH: 23
<212> TYPE: DNA
<213> ORGANISM: Artificial Sequence
<220> FEATURE:
<223> OTHER INFORMATION: Synthetic Oligonucleotide: mApril-2, mApril
      intron 5, Probe
```

<400> SEQUENCE: 18
tcacctcctg ggtttgattc cga                                           23

<210> SEQ ID NO 19
<211> LENGTH: 19
<212> TYPE: DNA
<213> ORGANISM: Artificial Sequence
<220> FEATURE:
<223> OTHER INFORMATION: Synthetic Oligonucleotide: hAPRIL-1a, hAPRIL
      exon 3, Forward

<400> SEQUENCE: 19
cctgcacctg gttcccatt                                                19

<210> SEQ ID NO 20
<211> LENGTH: 22
<212> TYPE: DNA
<213> ORGANISM: Artificial Sequence
<220> FEATURE:
<223> OTHER INFORMATION: Synthetic Oligonucleotide: hAPRIL-1a, hAPRIL
      exon 3, Reverse

<400> SEQUENCE: 20
agcccgagtt cctggttatt gc                                            22

<210> SEQ ID NO 21
<211> LENGTH: 20
<212> TYPE: DNA
<213> ORGANISM: Artificial Sequence
<220> FEATURE:
<223> OTHER INFORMATION: Synthetic Oligonucleotide: hAPRIL-1a, hAPRIL
      exon 3, Probe

<400> SEQUENCE: 21
aacgccacct ccaagggtga                                               20

<210> SEQ ID NO 22
<211> LENGTH: 21
<212> TYPE: DNA
<213> ORGANISM: Artificial Sequence
<220> FEATURE:
<223> OTHER INFORMATION: Synthetic Oligonucleotide: hAPRIL-2a, hAPRIL
      exon 6, 3'UTR, Forward

<400> SEQUENCE: 22
aggagcctcg ggtgtatcgt a                                             21

<210> SEQ ID NO 23
<211> LENGTH: 24
<212> TYPE: DNA
<213> ORGANISM: Artificial Sequence
<220> FEATURE:
<223> OTHER INFORMATION: Synthetic Oligonucleotide: hAPRIL-2a, hAPRIL
      exon 6, 3'UTR, Reverse

<400> SEQUENCE: 23
gcagggcttg atcagaaaga agag                                          24

<210> SEQ ID NO 24
<211> LENGTH: 22
<212> TYPE: DNA
<213> ORGANISM: Artificial Sequence
<220> FEATURE:
<223> OTHER INFORMATION: Synthetic Oligonucleotide: hAPRIL-2a, hAPRIL
      exon 6, 3'UTR, Probe

<400> SEQUENCE: 24

```
cctggtgtt ggtgttgcct ca                                              22

<210> SEQ ID NO 25
<211> LENGTH: 19
<212> TYPE: DNA
<213> ORGANISM: Artificial Sequence
<220> FEATURE:
<223> OTHER INFORMATION: primers specific for mouse April exon 1
      Synthetic Oligonucleotide:

<400> SEQUENCE: 25
agtcagagag ccagcccctt                                                19

<210> SEQ ID NO 26
<211> LENGTH: 22
<212> TYPE: DNA
<213> ORGANISM: Artificial Sequence
<220> FEATURE:
<223> OTHER INFORMATION: Synthetic Oligonucleotide: primers specific
      human APRIL exon 5

<400> SEQUENCE: 26
acatcggaat agagtctcct gc                                             22
```

METHOD FOR GENERATING A HUMANIZED TRANSGENIC MOUSE COMPRISING A HUMAN APRIL GENE

CROSS REFERENCE TO RELATED APPLICATIONS

This application is a divisional of U.S. patent application Ser. No. 14/537,320, filed Nov. 10, 2014, which claims the benefit of priority of U.S. Provisional Application No. 61/905,986, filed Nov. 19, 2013, the entire content of which is incorporated herein by reference.

INCORPORATION BY REFERENCE OF SEQUENCE LISTING

The Sequence Listing in the ASCII text file, named as 31016_6825_SEQ.txt of 32 KB bytes, created on Nov. 5, 2014, and submitted to the United States Patent and Trademark Office via EFS-Web, is incorporated herein by reference.

BACKGROUND

Autoimmunity results when an organism's natural mechanisms for preventing its immune system from attacking its own cells and tissues break down. Diseases, disorders and conditions caused by breakdown, and by the aberrant self-directed immune responses that result, are referred to as autoimmune diseases. Notable examples of autoimmune diseases, disorders and conditions include diabetes mellitus, systemic lupus erythematosus (SLE), rheumatoid arthritis (RA) and some allergies. Autoimmune diseases are estimated to be among the ten leading causes of death. Investment in the development of therapies for autoimmune diseases is in the multi-billion dollar range, and critical in vivo systems to test, develop and validate candidate therapeutics are necessary to ensure treatment safety and effectiveness. Further, such in vivo systems are necessary in determining if new treatments can sustain long term improvement in patients and, perhaps, can even provide cures for many diseases that remain unaddressed. Such in vivo systems also provide a source for assays in human hematopoietic and immune system related functions in vivo, identification of novel therapies and vaccines.

SUMMARY OF INVENTION

The present invention encompasses the recognition that it is desirable to engineer non-human animals to provide improved in vivo autoimmune disease systems to permit the testing, development and validation of new and existing candidate therapeutics. The present invention also encompasses the recognition that it is desirable to engineer non-human animals to permit improved activation and survival of human lymphocytes (e.g., B cells) post-immunization and post-engraftment of human hematopoietic stem cells or B cells from human donors. The present invention also encompasses the recognition that non-human animals having a humanized April gene and/or otherwise expressing, containing, or producing a human or humanized April protein are desirable, for example for use in engraftment of human hematopoietic stem cells or B cells from human donors.

In some embodiments, a non-human animal of the present invention expresses a April polypeptide comprising the extracellular portion of a human APRIL protein linked to the intracellular portion of a non-human April protein.

In some embodiments, an extracellular portion of a human APRIL protein is encoded by exons 2 to 6 of a human APRIL gene.

In some embodiments, exons 2 to 6 of a human APRIL gene are at least 50%, at least 55%, at least 60%, at least 65%, at least 70%, at least 75%, at least 80%, at least 85%, at least 90%, at least 95%, or at least 98% identical with exons 2 to 6 of a human APRIL gene that appears in Table 3. In some embodiments, exons 2 to 6 of a human APRIL gene are 100% identical with exons 2 to 6 of a human APRIL gene that appears in Table 3.

In some embodiments, a non-human animal of the present invention does not detectably express a full-length endogenous April protein. In some embodiments, the non-human animal is a rodent and does not detectably express a full-length rodent April protein. In some embodiments, the non-human animal is a mouse and does not detectably express a full-length mouse April protein whose sequence appears in Table 3.

In some embodiments, an April polypeptide of the present invention is expressed from a genetically modified April gene at an endogenous non-human April locus. In some certain embodiments, a genetically modified April gene comprises a non-human April exon 1. In some certain embodiments, a genetically modified April gene comprises a non-human April exon 6 in whole or in part. In some certain embodiments, a genetically modified April gene comprises a non-human April exon 1, a non-human April exon 6 in whole or in part, or a combination thereof. In various embodiments, a non-human April exon 6 in part comprises a non-human April 3'untranslated region (UTR) and a non-human April polyadenylation signal.

In some embodiments, the present invention provides a non-human animal comprising a genetically modified April gene that comprises one or more exons of a human APRIL gene (i.e., a humanized April gene) operably linked to a April promoter. In some embodiments, an April promoter of the present invention is a non-human April promoter. In some embodiments, an April promoter of the present invention is a human APRIL promoter.

In some embodiments, a humanized April gene of the present invention comprises exons 2 to 6 of a human APRIL gene. In some certain embodiments, a humanized April gene further comprises a non-human April exon 1. In some certain embodiments, a humanized April gene further comprises a non-human April exon 6 in whole or in part. In some certain embodiments, a humanized April gene comprises a non-human exon 1 and a non-human exon 6 in whole or in part. In various embodiments, a non-human April exon 6 in part comprises a non-human April 3'untranslated region (UTR) and a non-human April polyadenylation signal.

In some embodiments, exons 2 to 6 of a human APRIL gene are at least 50%, at least 55%, at least 60%0, at least 65%, at least 70%, at least 75%, at least 80%, at least 85%, at least 90%, at least 95%, or at least 98% identical with exons 2 to 6 of a human APRIL gene that appears in Table 3. In some embodiments, exons 2 to 6 of a human APRIL gene are 100% identical with exons 2 to 6 of a human APRIL gene that appears in Table 3.

In various embodiments, a non-human animal of the present invention is a rodent. In some certain embodiments, a rodent of the present invention is selected from a mouse or a rat.

In some embodiments, the present invention provides a humanized April locus (or gene) comprising one or more exons of a non-human April gene operably linked to one or more exons of a human APRIL gene.

In some embodiments, a humanized April locus (or gene) of the present invention comprises a non-human April exon 1 operably linked to human APRIL exons 2 to 6. In some certain embodiments, a humanized April locus (or gene) further comprises 5' and 3' non-human untranslated regions (UTRs) flanking the non-human April exon 1 and the human APRIL exon 6.

In some embodiments, the present invention provides an April polypeptide encoded by the humanized April locus (or gene) as described herein.

In some embodiments, the present invention provides a cell or tissue isolated from a non-human animal as described herein. In some embodiments, a cell is selected from a dendritic cell, lymphocyte (e.g., a B or T cell), macrophage and a monocyte. In some embodiments, a tissue is selected from adipose, bladder, brain, breast, bone marrow, eye, heart, intestine, kidney, liver, lung, lymph node, muscle, pancreas, plasma, serum, skin, spleen, stomach, thymus, testis, ovum, and/or a combination thereof.

In some embodiments, the present invention provides an isolated non-human (e.g., rodent) cell or tissue whose genome includes an April gene (or locus) comprising one or more exons of a non-human April gene operably linked to one or more exons of a human APRIL gene. In some certain embodiments, the present invention provides an isolated non-human (e.g., rodent) cell or tissue whose genome includes an April gene (or locus) comprising non-human April exons 1 and 6, in whole or in part, operably linked to human APRIL exons 2 to 6, wherein the April gene (or locus) further comprises 5' and 3' non-human untranslated regions (UTRs) flanking the non-human April exon 1 and the human APRIL exon 6. In some embodiments, an April gene (or locus) comprises a sequence that encodes an April polypeptide that comprises residues 87 to 250 of a human APRIL protein.

In some embodiments, the present invention provides a non-human embryonic stem (ES) cell whose genome comprises an April gene (or locus) as described herein. In some certain embodiments, the ES cell comprises an April gene that encodes the extracellular portion of a human APRIL protein linked to the intracellular portion of a mouse April protein. In some certain embodiments, the ES cell comprises an April gene that comprises exons 2 to 6 of a human APRIL gene. In some certain embodiments, the ES cell is a rodent ES cell. In some embodiments, a non-human ES cell of the present invention is a mouse or rat ES cell.

In some embodiments, the present invention provides the use of a non-human embryonic stem cell as described herein to make a non-human animal. In some certain embodiments, a non-human embryonic stem cell is murine and is used to make a mouse comprising an April gene as described herein.

In some embodiments, the present invention provides a non-human embryo comprising, made from, obtained from, or generated from a non-human embryonic stem cell comprises an April gene as described herein. In some embodiments, a non-human embryo of the present invention is a rodent embryo. In some embodiments, a rodent embryo as described herein is a mouse or rat embryo.

In some embodiments, the present invention provides a method of making a non-human animal that expresses an April protein from a humanized April gene at an endogenous April locus, wherein the April protein comprises a human sequence, the method comprising the steps of targeting an endogenous April gene (or locus) in a non-human embryonic stem (ES) cell with a genomic fragment comprising a human nucleotide sequence that encodes a human APRIL protein in whole or in part, obtaining a modified non-human embryonic stem (ES) cell comprising a humanized April gene at an endogenous April locus that comprises said human sequence, and creating a non-human animal using said modified embryonic stem (ES) cell.

In some embodiments, said human nucleotide sequence comprises exons 2 to 6 of a human APRIL gene. In some embodiments, said human nucleotide sequence comprises exons 2 to 6 of a human APRIL gene that are at least 50%, at least 55%, at least 60%, at least 65%, at least 70%, at least 75%, at least 80%, at least 85%, at least 90%, at least 95%, or at least 98% identical with exons 2 to 6 of a human APRIL gene that appears in Table 3. In some certain embodiments, said human nucleotide sequence comprises exons 2 to 6 of a human APRIL gene that are 100% identical with exons 2 to 6 of a human APRIL gene that appears in Table 3.

In some embodiments, said human nucleotide sequence encodes amino acid residues 87 to 250 of a human APRIL protein. In embodiments, said human nucleotide sequence encodes amino acid residues 87 to 250 of a human APRIL protein that are at least 50%, at least 55%, at least 60%, at least 65%, at least 70%, at least 75%, at least 80%, at least 85%, at least 90%, at least 95%, or at least 98% identical with amino acid residues 87 to 250 of a human APRIL protein that appears in Table 3. In some certain embodiments, said human nucleotide sequence encodes amino acid residues 87 to 250 of a human APRIL protein that are 100% identical with amino acid residues 87 to 250 of a human APRIL protein that appears in Table 3.

In some embodiments, the present invention provides a mouse or a rat made by, or obtained (or obtainable) from, a method as described herein. In some certain embodiments, a mouse or a rat made by, or obtained (or obtainable) from, a method as described herein do not detectably express a full-length endogenous (e.g., mouse or rat) April protein.

In some embodiments, the present invention provides a method of providing a mouse whose genome includes an April gene that encodes the extracellular portion of a human APRIL protein linked to the intracellular portion of a mouse April protein, the method comprising modifying the genome of a mouse so that it comprises an April gene that encodes the extracellular portion of a human APRIL protein linked to the intracellular portion of a mouse April protein thereby providing said mouse. In some embodiments, an April gene is an April gene as described herein. In some embodiments, an April gene is one that encodes a protein whose sequence reflects a humanized April protein that appears in Table 3. In some certain embodiments, an April gene comprises exons 2 to 6 a human APRIL gene.

In various embodiments, a humanized April gene of the present invention comprises exons 2, 3, 4, 5 and 6 of a human APRIL gene. In various embodiments, an extracellular portion of a humanized April protein of the present invention comprises amino acids corresponding to residues 87 to 250 of a human APRIL protein that appears in Table 3. In some certain embodiments, a humanized April protein of the present invention comprises a sequence of a humanized April protein that appears in Table 3. In various embodiments, a humanized April gene of the present invention is operably linked to a mouse April promoter.

In some embodiments, the present invention provides a method of engrafting human cells into a mouse, the method comprising the steps of providing a mouse whose genome comprises an April gene that encodes the extracellular portion of a human APRIL protein linked to the intracellular portion of a mouse April protein (as described herein), and transplanting one or more human cells into the mouse. In some certain embodiments, the method further comprises a step of assaying engraftment of the one or more human cells in the mouse. In some certain embodiments, the step of assaying comprises comparing the engraftment of the one or more human cells to the engraftment in one or more wild-type mice or in one or more mice whose genome does not comprise a April gene that encodes the extracellular portion of a human APRIL protein linked to the intracellular portion of a mouse April protein.

In some certain embodiments, the human cells are hematopoietic stem cells. In some certain embodiments, the human cells are human B cells.

In some embodiments, the human cells are transplanted intravenously. In some embodiments, the human cells are transplanted intraperitoneally. In some embodiments, the human cells are transplanted subcutaneously.

In some embodiments, the present invention provides methods for identification or validation of a drug or vaccine, the method comprising the steps of delivering a drug or vaccine to a non-human animal as described herein, and monitoring one or more of the immune response to the drug or vaccine, the safety profile of the drug or vaccine, or the effect on a disease or condition. In some embodiments, monitoring the safety profile includes determining if the non-human animal exhibits a side effect or adverse reaction as a result of delivering the drug or vaccine. In some embodiments, a side effect or adverse reaction is selected from morbidity, mortality, alteration in body weight, alteration of the level of one or more enzymes (e.g., liver), alteration in the weight of one or more organs, loss of function (e.g., sensory, motor, organ, etc.), increased susceptibility to one or more diseases, alterations to the genome of the non-human animal, increase or decrease in food consumption and complications of one or more diseases.

In some embodiments, the present invention provides use of a non-human animal of the present invention in the development of a drug or vaccine for use in medicine, such as use as a medicament.

In various embodiments, non-human animals of the present invention are rodents, preferably a mouse or a rat.

As used in this application, the terms "about" and "approximately" are used as equivalents. Any numerals used in this application with or without about/approximately are meant to cover any normal fluctuations appreciated by one of ordinary skill in the relevant art.

Other features, objects, and advantages of the present invention are apparent in the detailed description that follows. It should be understood, however, that the detailed description, while indicating embodiments of the present invention, is given by way of illustration only, not limitation. Various changes and modifications within the scope of the invention will become apparent to those skilled in the art from the detailed description.

BRIEF DESCRIPTION OF THE DRAWING

The Drawing included herein, which is composed of the following Figures, is for illustration purposes only not for limitation.

DEFINITIONS

Figure 1:
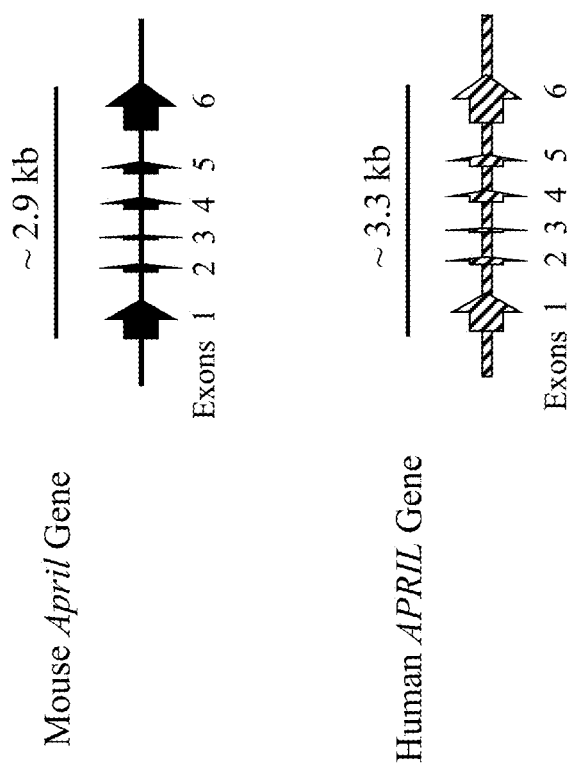
FIG. 1 shows a diagram, not to scale, of the genomic organization of an exemplary non-human (e.g., mouse) and human A PRoliferation-Inducing Ligand (APRIL) genes. Exons are numbered beneath each exon.

This invention is not limited to particular methods, and experimental conditions described, as such methods and conditions may vary. It is also to be understood that the terminology used herein is for the purpose of describing particular embodiments only, and is not intended to be limiting, since the scope of the present invention is defined by the claims.

Unless defined otherwise, all terms and phrases used herein include the meanings that the terms and phrases have attained in the art, unless the contrary is clearly indicated or clearly apparent from the context in which the term or phrase is used. Although any methods and materials similar or equivalent to those described herein can be used in the practice or testing of the present invention, particular methods and materials are now described. All publications mentioned are hereby incorporated by reference.

The term "approximately" as applied herein to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 900, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

The term "biologically active" as used herein refers to a characteristic of any agent that has activity in a biological system, in vitro or in vivo (e.g., in an organism). For instance, an agent that, when present in an organism, has a biological effect within that organism, is considered to be biologically active. In particular embodiments, where a protein or polypeptide is biologically active, a portion of that protein or polypeptide that shares at least one biological activity of the protein or polypeptide is typically referred to as a "biologically active" portion.

The term "comparable", as used herein, refers to two or more agents, entities, situations, sets of conditions, etc. that may not be identical to one another but that are sufficiently similar to permit comparison there between so that conclusions may reasonably be drawn based on differences or similarities observed. Those of ordinary skill in the art will understand, in context, what degree of identity is required in any given circumstance for two or more such agents, entities, situations, sets of conditions, etc. to be considered comparable.

The term "conservative" as used herein to describe a conservative amino acid substitution refers to substitution of an amino acid residue by another amino acid residue having a side chain R group with similar chemical properties (e.g., charge or hydrophobicity). In general, a conservative amino acid substitution will not substantially change the functional properties of interest of a protein, for example, the ability of a receptor to bind to a ligand. Examples of groups of amino acids that have side chains with similar chemical properties include aliphatic side chains such as glycine, alanine, valine, leucine, and isoleucine; aliphatic-hydroxyl side chains such as serine and threonine; amide-containing side chains such as asparagine and glutamine; aromatic side chains such as phenylalanine, tyrosine, and tryptophan; basic side chains such as lysine, arginine, and histidine; acidic side chains such as aspartic acid and glutamic acid; and, sulfur-containing side chains such as cysteine and methionine. Conservative amino acids substitution groups include, for example, valine/leucine/isoleucine, phenylalanine/tyrosine, lysine/arginine, alanine/valine, glutamate/aspartate, and asparagine/glutamine. In some embodiments, a conservative amino acid substitution can be substitution of any native residue in a protein with alanine, as used in, for example, alanine scanning mutagenesis. In some embodiments, a conservative substitution is one that that has a positive value in the PAM250 log-likelihood matrix disclosed in Gonnet et al. (1992) Exhaustive Matching of the Entire Protein Sequence Database, Science 256:1443-45, hereby incorporated by reference. In some embodiments, a substitution is deemed to be "moderately conservative" if it has a nonnegative value in the PAM250 log-likelihood matrix.

The term "disruption" as used herein refers to the result of an event that interrupts (e.g., via homologous recombination) a DNA molecule. In some embodiments, a disruption may achieve or represent a deletion, insertion, inversion, modification, replacement, substitution, or any combination thereof, of a DNA sequence(s). In some embodiments, a disruption may achieve or present introduction of a mutation, such as a missense, nonsense, or frame-shift mutation, or any combination thereof, in a coding sequence(s) in DNA. In some embodiments, a disruption may occur in a gene or gene locus endogenous to a cell. In some embodiments, insertions may include the insertion of entire genes or fragments of genes, e.g. exons, into an endogenous site in a cell or genome. In some embodiments, insertions may introduce sequences that are of an origin other than that of an endogenous sequence into which they are inserted. In some embodiments, a disruption may increase expression and/or activity of a gene or gene product (e.g., of a protein encoded by a gene). In some embodiments, a disruption may decrease expression and/or activity of a gene or gene product. In some embodiments, a disruption may alter sequence of a gene or gene product (e.g., an encoded protein). In some embodiments, a disruption may truncate or fragment a gene or gene product (e.g., an encoded protein). In some embodiments, a disruption may extend a gene or gene product; in some such embodiments, a disruption may achieve assembly of a fusion protein. In some embodiments, a disruption may affect level but not activity of a gene or gene product. In some embodiments, a disruption may affect activity but not level of a gene or gene product. In some embodiments, a disruption may have no significant effect on level of a gene or gene product. In some embodiments, a disruption may have no significant effect on activity of a gene or gene product. In some embodiments, a disruption may have no significant effect on either level or activity of a gene or gene product.

The phrase "endogenous locus" or "endogenous gene" as used herein refers to a genetic locus found in a parent or reference organism prior to introduction of a disruption (e.g., deletion, insertion, inversion, modification, replacement, substitution, or a combination thereof as described herein). In some embodiments, an endogenous locus has a sequence found in nature. In some embodiments, an endogenous locus is wild type. In some embodiments, a reference organism that contains an endogenous locus as described herein is a wild-type organism. In some embodiments, a reference organism that contains an endogenous locus as described herein is an engineered organism. In some embodiments, the reference organism is a laboratory-bred organism (whether wild-type or engineered).

The phrase "endogenous promoter" refers to a promoter that is naturally associated, e.g., in a wild-type organism, with an endogenous gene.

The term "heterologous" as used herein refers to an agent or entity from a different source. For example, when used in reference to a polypeptide, gene, or gene product or present in a particular cell or organism, the term clarifies that the relevant polypeptide, gene, or gene product 1) was engineered by the hand of man; 2) was introduced into the cell or organism (or a precursor thereof) through the hand of man (e.g., via genetic engineering); and/or 3) is not naturally produced by or present in the relevant cell or organism (e.g., the relevant cell type or organism type).

The term "host cell", as used herein, refers to a cell into which a heterologous (e.g., exogenous) nucleic acid or protein has been introduced. Persons of skill upon reading this disclosure will understand that such terms refer not only to the particular subject cell, but also is used to refer to progeny of that cell. Because certain modifications may occur in succeeding generations due to either mutation or environmental influences, such progeny may not, in fact, be identical to the parent cell, but are still understood by those skilled in the art to be included within the scope of the term "host cell" as used herein. In some embodiments, a host cell is or comprises a prokaryotic or eukaryotic cell. In general, a host cell is any cell that is suitable for receiving and/or producing a heterologous nucleic acid or protein, regardless of the Kingdom of life to which the cell is designated. Exemplary cells that may be utilized as host cells in accordance with the present disclosure include those of prokaryotes and eukaryotes (single-cell or multiple-cell), bacterial cells (e.g., strains of *E. coli*, *Bacillus* spp., *Streptomyces* spp., etc.), mycobacteria cells, fungal cells, yeast cells (e.g.,

*S. cerevisiae, S. pombe, P. pastoris, P. methanolica*, etc.), plant cells, insect cells (e.g., SF-9, SF-21, baculovirus-infected insect cells, *Trichoplusia ni*, etc.), non-human animal cells, human cells, or cell fusions such as, for example, hybridomas or quadromas. In some embodiments, the cell is a human, monkey, ape, hamster, rat, or mouse cell. In some embodiments, the cell is eukaryotic and is selected from the following cells: CHO (e.g., CHO K1, DXB-11 CHO, Veggie-CHO), COS (e.g., COS-7), retinal cell, Vero, CV1, kidney (e.g., HEK293, 293 EBNA, MSR 293, MDCK, HaK, BHK), HeLa, HepG2, WI38, MRC 5, Colo205, HB 8065, HL-60, (e.g., BHK21), Jurkat, Daudi, A431 (epidermal), CV-1, U937, 3T3, L cell, C127 cell, SP2/0, NS-0, MMT 060562, Sertoli cell, BRL 3A cell, HT1080 cell, myeloma cell, tumor cell, and a cell line derived from an aforementioned cell. In some embodiments, the cell comprises one or more viral genes, e.g., a retinal cell that expresses a viral gene (e.g., a PER.C6™ cell). In some embodiments, a host cell is or comprises an isolated cell. In some embodiments, a host cell is part of a tissue. In some embodiments, a host cell is part of an organism.

The term "humanized", is used herein in accordance with its art-understood meaning to refer to nucleic acids or proteins whose structures (i.e., nucleotide or amino acid sequences) include portions that correspond substantially or identically with versions of the relevant nucleic acids or proteins that are found in nature in non-human animals and that are distinguishable from corresponding versions that are found in nature in humans, and also include portions whose structures differ from those present in the non-human-animal versions and instead correspond more closely with comparable structures found in the human versions. In some embodiments, a "humanized" gene is one that encodes a polypeptide having substantially the amino acid sequence as that of a human polypeptide (e.g., a human protein or portion thereof—e.g., characteristic portion thereof). To give but one example, in the case of a membrane receptor, a "humanized" gene may encode a polypeptide with an extracellular portion whose amino acid sequence is identical or substantially identical to that of a human extracellular portion and whose remaining sequence is identical or substantially identical to that of a non-human (e.g., mouse) polypeptide. In some embodiments, a humanized gene comprises at least a portion of an DNA sequence of a human gene. In some embodiment, a humanized gene comprises an entire DNA sequence found in a human gene. In some embodiments, a humanized protein has an amino acid sequence that comprises a portion that appears in a human protein. In some embodiments, a humanized protein has an amino acid sequence whose entire sequence is found in a human protein. In some embodiments (including, for example, some in which a humanized protein has an amino acid sequence whose entire sequence is found in a human protein), a humanized protein is expressed from an endogenous locus of a non-human animal, which endogenous locus corresponds to the homolog or ortholog of the relevant human gene encoding the protein.

The term "identity" as used herein in connection with a comparison of sequences, refers to identity as determined by any of a number of different algorithms known in the art that can be used to measure nucleotide and/or amino acid sequence identity. In some embodiments, identities as described herein are determined using a ClustalW v. 1.83 (slow) alignment employing an open gap penalty of 10.0, an extend gap penalty of 0.1, and using a Gonnet similarity matrix (MACVECTOR™ 10.0.2, MacVector Inc., 2008). As used herein, the term "identity" refers to the overall relatedness between polymeric molecules, e.g., between nucleic acid molecules (e.g., DNA molecules and/or RNA molecules) and/or between polypeptide molecules. In some embodiments, polymeric molecules are considered to be "substantially identical" to one another if their sequences are at least 25%, 30%, 35%, 40%, 45%, 50%, 55%, 60%, 65%, 70%, 75%, 80%, 85%, 90%, 95%, or 99% identical. As will be understood by those skilled in the art, a variety of algorithms are available that permit comparison of sequences in order to determine their degree of homology, including by permitting gaps of designated length in one sequence relative to another when considering which residues "correspond" to one another in different sequences. Calculation of the percent identity between two nucleic acid sequences, for example, can be performed by aligning the two sequences for optimal comparison purposes (e.g., gaps can be introduced in one or both of a first and a second nucleic acid sequences for optimal alignment and non-corresponding sequences can be disregarded for comparison purposes). In certain embodiments, the length of a sequence aligned for comparison purposes is at least 30%, at least 400, at least 50%, at least 60%, at least 700, at least 80%, at least 90%, at least 95%, or substantially 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. Representative algorithms and computer programs useful in determining the percent identity between two nucleotide sequences include, for example, the algorithm of Meyers and Miller (CABIOS, 1989, 4: 11-17), which has been incorporated into the ALIGN program (version 2.0) using a PAM120 weight residue table, a gap length penalty of 12 and a gap penalty of 4. The percent identity between two nucleotide sequences can, alternatively, be determined for example using the GAP program in the GCG software package using an NWSgapdna.CMP matrix.

The term "isolated", as used herein, refers to a substance and/or entity that has been (1) separated from at least some of the components with which it was associated when initially produced (whether in nature and/or in an experimental setting), and/or (2) designed, produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99%, pure. As used herein, a substance is "pure" if it is substantially free of other components. In some embodiments, as will be understood by those skilled in the art, a substance may still be considered "isolated" or even "pure", after having been combined with certain other components such as, for example, one or more carriers or excipients (e.g., buffer, solvent, water, etc.); in such embodiments, percent isolation or purity of the substance is calculated without including such carriers or excipients. To give but one example, in some embodiments, a biological polymer such as a polypeptide or polynucleotide that occurs in nature is considered to be "isolated" when, a) by virtue of its origin or source of derivation is not associated with some or all of the components that accompany it in its native state in nature; b) it is substantially free of other polypeptides or nucleic acids of the same species from the species that produces it in nature; c) is expressed by or is otherwise in association with components from a cell or other expression system that is not of the species that produces it in nature. Thus, for instance, in some embodiments, a polypeptide that is chemically synthesized or is synthesized in a cellular system different from that which produces it in nature is considered to be an "isolated" polypeptide. Alternatively or additionally, in some embodiments, a polypeptide that has been subjected to one or more purification techniques may be considered to be an "isolated" polypeptide to the extent that it has been separated from other components a) with which it is associated in nature; and/or b) with which it was associated when initially produced.

The phrase "non-human animal" as used herein refers to a vertebrate organism that is not a human. In some embodiments, a non-human animal is acyclostome, a bony fish, a cartilaginous fish (e.g., a shark or a ray), an amphibian, a reptile, a mammal, or a bird. In some embodiments, a non-human mammal is a primate, a goat, a sheep, a pig, a dog, a cow, or a rodent. In some embodiments, a non-human animal is a rodent such as a rat or a mouse.

The phrase "nucleic acid", as used herein, in its broadest sense, refers to any compound and/or substance that is or can be incorporated into an oligonucleotide chain. In some embodiments, a nucleic acid is a compound and/or substance that is or can be incorporated into an oligonucleotide chain via a phosphodiester linkage. As will be clear from context, in some embodiments, "nucleic acid" refers to one or more individual nucleic acid residues (e.g., nucleotides and/or nucleosides); in some embodiments, "nucleic acid" refers to an oligonucleotide chain comprising individual nucleic acid residues. In some embodiments, a "nucleic acid" is or comprises RNA; in some embodiments, a "nucleic acid" is or comprises DNA. In some embodiments, a nucleic acid is, comprises, or consists of one or more natural nucleic acid residues. In some embodiments, a nucleic acid is, comprises, or consists of one or more analogs of a natural nucleic acid residue. In some embodiments, a nucleic acid analog differs from a natural nucleic acid residue in that it does not utilize a phosphodiester backbone. For example, in some embodiments, a nucleic acid is, comprises, or consists of one or more "peptide nucleic acids", which are known in the art and have peptide bonds instead of phosphodiester bonds in the backbone, are considered within the scope of the present invention. Alternatively or additionally, in some embodiments, a nucleic acid has one or more phosphorothioate and/or 5'-N-phosphoramidite linkages rather than phosphodiester bonds. In some embodiments, a nucleic acid is, comprises, or consists of one or more natural nucleosides (e.g., adenosine, thymidine, guanosine, cytidine, uridine, deoxyadenosine, deoxythymidine, deoxyguanosine, and deoxycytidine). In some embodiments, a nucleic acid is, comprises, or consists of one or more nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, 2-thiocytidine, methylated bases, intercalated bases, and combinations thereof). In some embodiments, a nucleic acid comprises one or more modified sugars (e.g., 2'-fluororibose, ribose, 2'-deoxyribose, arabinose, and hexose) as compared with those in natural nucleic acids (i.e., comprises one or more analogs of a natural nucleoside sugar). In some embodiments, a nucleic acid has a nucleotide sequence that encodes a functional gene product such as an RNA or protein. In some embodiments, a nucleic acid has a nucleotide sequence that includes one or more introns. Those of ordinary skill in the art will appreciate that a variety of technologies are available and known in the art for the production of nucleic acids. For example, in some embodiments, nucleic acids are prepared by a method selected from the group consisting of isolation from a natural source, enzymatic synthesis by polymerization based on a complementary template (in vivo or in vitro), reproduction in a recombinant cell or system, chemical synthesis, and a combination thereof. In some embodiments, a nucleic acid is at least 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 20, 225, 250, 275, 300, 325, 350, 375, 400, 425, 450, 475, 500, 600, 700, 800, 900, 1000, 1500, 2000, 2500, 3000, 3500, 4000, 4500, 5000 or more residues long. In some embodiments, a nucleic acid is single stranded; in some embodiments, a nucleic acid is partially or fully double stranded (i.e., comprises at least two individual nucleic acid strands whose sequences include complementary elements that hybridize to one another). In some embodiments a nucleic acid has a nucleotide sequence comprising at least one element that encodes, or is the complement of a sequence that encodes, a polypeptide. In some embodiments, a nucleic acid has enzymatic activity.

The phrase "operably linked", as used herein, refers to a physical juxtaposition (e.g., in three-dimensional space) of components or elements that interact, directly or indirectly with one another, or otherwise coordinate with each other to participate in a biological event, which juxtaposition achieves or permits such interaction and/or coordination. To give but one example. A control sequence (e.g., an expression control sequence) in a nucleic acid is said to be "operably linked" to a coding sequence when it is located relative to the coding sequence such that its presence or absence impacts expression and/or activity of the coding sequence. In many embodiments, "operable linkage" involves covalent linkage of relevant components or elements with one another. Those skilled in the art will readily appreciate, however, that in some embodiments, covalent linkage is not required to achieve effective operable linkage. For example, in some embodiments, nucleic acid control sequences that are operably linked with coding sequences that they control are contiguous with the gene of interest. Alternatively or additionally, in some embodiments, one or more such control sequences acts in trans or at a distance to control a coding sequence of interest. In some embodiments, the term "expression control sequence" as used herein refers to polynucleotide sequences which are necessary and/or sufficient to effect the expression and processing of coding sequences to which they are ligated. In some embodiments, expression control sequences may be or comprise appropriate transcription initiation, termination, promoter and/or enhancer sequences; efficient RNA processing signals such as splicing and polyadenylation signals; sequences that stabilize cytoplasmic mRNA; sequences that enhance translation efficiency (e.g., Kozak consensus sequence); sequences that enhance protein stability; and/or, in some embodiments, sequences that enhance protein secretion. In some embodiments, one or more control sequences is preferentially or exclusively active in a particular host cell or organism, or type thereof. To give but one example, in prokaryotes, control sequences typically include promoter, ribosomal binding site, and transcription termination sequence; in eukaryotes, in many embodiments, control sequences typically include promoters, enhancers, and/or transcription termination sequences. Those of ordinary skill in the art will appreciate from context that, in many embodiments, the term "control sequences" refers to components whose presence is essential for expression and processing, and in some embodiments includes components whose presence is advantageous for expression (including, for example, leader sequences, targeting sequences, and/or fusion partner sequences).

The term "polypeptide", as used herein, refers to any polymeric chain of amino acids. In some embodiments, a polypeptide has an amino acid sequence that occurs in nature. In some embodiments, a polypeptide has an amino acid sequence that does not occur in nature. In some embodiments, a polypeptide has an amino acid sequence that is engineered in that it is designed and/or produced through action of the hand of man.

The term "recombinant", as used herein, is intended to refer to polypeptides (e.g., signal-regulatory proteins as described herein) that are designed, engineered, prepared, expressed, created or isolated by recombinant means, such as polypeptides expressed using a recombinant expression vector transfected into a host cell, polypeptides isolated from a recombinant, combinatorial human polypeptide library (Hoogenboom H. R., (1997) TIB Tech. 15:62-70; Azzazy H., and Highsmith W. E., (2002) Clin. Biochem. 35:425-445; Gavilondo J. V., and Larrick J. W. (2002) BioTechniques 29:128-145; Hoogenboom H., and Chames P. (2000) Immunology Today 21:371-378), antibodies isolated from an animal (e.g., a mouse) that is transgenic for human immunoglobulin genes (see e.g., Taylor, L. D., et al. (1992) Nucl. Acids Res. 20:6287-6295; Kellermann S-A., and Green L. L. (2002) Current Opinion in Biotechnology 13:593-597; Little M. et al (2000) Immunology Today 21:364-370) or polypeptides prepared, expressed, created or isolated by any other means that involves splicing selected sequence elements to one another. In some embodiments, one or more of such selected sequence elements is found in nature. In some embodiments, one or more of such selected sequence elements is designed in silico. In some embodiments, one or more such selected sequence elements results from mutagenesis (e.g., in vivo or in vitro) of a known sequence element, e.g., from a natural or synthetic source. For example, in some embodiments, a recombinant polypeptide is comprised of sequences found in the genome of a source organism of interest (e.g., human, mouse, etc.). In some embodiments, a recombinant polypeptide has an amino acid sequence that resulted from mutagenesis (e.g., in vitro or in vivo, for example in a non-human animal), so that the amino acid sequences of the recombinant polypeptides are sequences that, while originating from and related to polypeptides sequences, may not naturally exist within the genome of a non-human animal in vivo.

The term "replacement" is used herein to refer to a process through which a "replaced" nucleic acid sequence (e.g., a gene) found in a host locus (e.g., in a genome) is removed from that locus and a different, "replacement" nucleic acid is located in its place. In some embodiments, the replaced nucleic acid sequence and the replacement nucleic acid sequences are comparable to one another in that, for example, they are homologous to one another and/or contain corresponding elements (e.g., protein-coding elements, regulatory elements, etc.). In some embodiments, a replaced nucleic acid sequence includes one or more of a promoter, an enhancer, a splice donor site, a splice receiver site, an intron, an exon, an untranslated region (UTR); in some embodiments, a replacement nucleic acid sequence includes one or more coding sequences. In some embodiments, a replacement nucleic acid sequence is a homolog of the replaced nucleic acid sequence. In some embodiments, a replacement nucleic acid sequence is an ortholog of the replaced sequence. In some embodiments, a replacement nucleic acid sequence is or comprises a human nucleic acid sequence. In some embodiments, including where the replacement nucleic acid sequence is or comprises a human nucleic acid sequence, the replaced nucleic acid sequence is or comprises a rodent sequence (e.g., a mouse sequence). The nucleic acid sequence so placed may include one or more regulatory sequences that are part of source nucleic acid sequence used to obtain the sequence so placed (e.g., promoters, enhancers, 5'- or 3'-untranslated regions, etc.). For example, in various embodiments, the replacement is a substitution of an endogenous sequence with a heterologous sequence that results in the production of a gene product from the nucleic acid sequence so placed (comprising the heterologous sequence), but not expression of the endogenous sequence; the replacement is of an endogenous genomic sequence with a nucleic acid sequence that encodes a protein that has a similar function as a protein encoded by the endogenous sequence (e.g., the endogenous genomic sequence encodes a April protein, and the DNA fragment encodes one or more human APRIL proteins). In various embodiments, an endogenous gene or fragment thereof is replaced with a corresponding human gene or fragment thereof. A corresponding human gene or fragment thereof is a human gene or fragment that is an ortholog of, or is substantially similar or the same in structure and/or function, as the endogenous gene or fragment thereof that is replaced.

The phrase "a proliferation-inducing ligand" or "APRIL" or "April" as used herein refers to an tumor necrosis family ligand, i.e., a TNF family ligand. APRIL is a type II membrane-bound protein, which can be released as a soluble ligand upon proteolytic processing at a furin cleavage site. APRIL is expressed on the surface of a cell and serves as a regulatory protein involved in interactions between membrane surface proteins on immune cells, e.g., B cells. Several variants, including some resulting from alternative splicing events, have been described in human subjects as well as in rodents. By way of illustration, nucleotide and amino acid sequences of mouse and human APRIL genes are provided in Table 3. Persons of skill upon reading this disclosure will recognize that one or more endogenous April genes in a genome (or all) can be replaced by one or more heterologous April genes (e.g., polymorphic variants, subtypes or mutants, genes from another species, humanized forms, etc.).

An "APRIL-expressing cell" as used herein refers to a cell that expresses a proliferation-inducing ligand. In some embodiments, an APRIL-expressing cell expresses a proliferation-inducing ligand on its surface. In some embodiments, an APRIL protein is expressed on the surface of the cell in an amount sufficient to mediate cell-to-cell interactions via the APRIL protein expressed on the surface of the cell. In some embodiments, a APRIL-expressing cell express a proliferation-inducing ligand in soluble form (i.e., not on the surface of a cell). Exemplary APRIL-expressing cells include dendritic cells, macrophages, monocytes and T cells.

APRIL-expressing cells regulate the interaction of immune cells to regulate the B cell responses to various foreign antigens or pathogens, including class switching to specific antibody isotypes. In some embodiments, non-human animals of the present invention demonstrate immune cell regulation via humanized April ligands expressed on the surface of one more cells of the non-human animal. In some embodiments, non-human animals of the present invention promote the long-term survival of B cells in non-human animals that comprise heterologous hematopoietic stem cells (e.g., human). In some embodiments, non-human animals of the present invention promote the long-term survival of antigen-specific B cells in non-human animals that comprise heterologous hematopoietic stem cells (e.g., human).

The term "substantially" as used herein refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

The phrase "substantial homology" as used herein refers to a comparison between amino acid or nucleic acid sequences. As will be appreciated by those of ordinary skill in the art, two sequences are generally considered to be "substantially homologous" if they contain homologous residues in corresponding positions. Homologous residues may be identical residues. Alternatively, homologous residues may be non-identical residues will appropriately similar structural and/or functional characteristics. For example, as is well known by those of ordinary skill in the art, certain amino acids are typically classified as "hydrophobic" or "hydrophilic" amino acids, and/or as having "polar" or "non-polar" side chains. Substitution of one amino acid for another of the same type may often be considered a "homologous" substitution. Typical amino acid categorizations are summarized in Table 1 and 2.

As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, *J. Mol. Biol.*, 215(3): 403-410, 1990; Altschul, et al., *Methods in Enzymology*; Altschul, et al., "Gapped BLAST and PSI-BLAST: a new generation of protein database search programs", *Nucleic Acids Res.* 25:3389-3402, 1997; Baxevanis, et al., *Bioinformatics: A Practical Guide to the Analysis of Genes and Proteins*, Wiley, 1998; and Misener, et al., (eds.), *Bioinformatics Methods and Protocols* (Methods in Molecular Biology, Vol. 132), Humana Press, 1999. In addition to identifying homologous sequences, the programs mentioned above typically provide an indication of the degree of homology. In some embodiments, two sequences are considered to be substantially homologous if at least 50%, 55%, 60%. 65%, 70%, 75%, 80%, 85%, 90%, 91%. 92%, 93%, 94%, 95%, 96%. 97%, 98%, 99% or more of their corresponding residues are homologous over a relevant stretch of residues. In some embodiments, the relevant stretch is a complete sequence. In some embodiments, the relevant stretch is at least 9, 10, 11, 12, 13, 14, 15, 16, 17 or more residues. In some embodiments, the relevant stretch includes contiguous residues along a complete sequence. In some embodiments, the relevant stretch includes discontinuous residues along a complete sequence. In some embodiments, the relevant stretch is at least 10, 15, 20, 25, 30, 35, 40, 45, 50, or more residues.

TABLE 1

| Alanine | Ala | A | nonpolar | neutral | 1.8 |
| Arginine | Arg | R | polar | positive | −4.5 |
| Asparagine | Asn | N | polar | neutral | −3.5 |
| Aspartic acid | Asp | D | polar | negative | −3.5 |
| Cysteine | Cys | C | nonpolar | neutral | 2.5 |
| Glutamic acid | Glu | E | polar | negative | −3.5 |
| Glutamine | Gln | Q | polar | neutral | −3.5 |
| Glycine | Gly | G | nonpolar | neutral | −0.4 |
| Histidine | His | H | polar | positive | −3.2 |
| Isoleucine | Ile | I | nonpolar | neutral | 4.5 |
| Leucine | Leu | L | nonpolar | neutral | 3.8 |
| Lysine | Lys | K | polar | positive | −3.9 |
| Methionine | Met | M | nonpolar | neutral | 1.9 |
| Phenylalanine | Phe | F | nonpolar | neutral | 2.8 |
| Proline | Pro | P | nonpolar | neutral | −1.6 |
| Serine | Ser | S | polar | neutral | −0.8 |
| Threonine | Thr | T | polar | neutral | −0.7 |
| Tryptophan | Trp | W | nonpolar | neutral | −0.9 |
| Tyrosine | Tyr | Y | polar | neutral | −1.3 |
| Valine | Val | V | nonpolar | neutral | 4.2 |

TABLE 2

| Ambiguous Amino Acids | 3-Letter | 1-Letter |
| --- | --- | --- |
| Asparagine or aspartic acid | Asx | B |
| Glutamine or glutamic acid | Glx | Z |
| Leucine or Isoleucine | Xle | J |
| Unspecified or unknown amino acid | Xaa | X |

The phrase "substantial identity" as used herein refers to a comparison between amino acid or nucleic acid sequences. As will be appreciated by those of ordinary skill in the art, two sequences are generally considered to be "substantially identical" if they contain identical residues in corresponding positions. As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, *J. Mol. Biol.*, 215(3): 403-410, 1990; Altschul, et al., *Methods in Enzymology*; Altschul et al., *Nucleic Acids Res.* 25:3389-3402, 1997; Baxevanis et al., *Bioinformatics: A Practical Guide to the Analysis of Genes and Proteins*, Wiley, 1998; and Misener, et al., (eds.), *Bioinformatics Methods and Protocols* (Methods in Molecular Biology, Vol. 132), Humana Press, 1999. In addition to identifying identical sequences, the programs mentioned above typically provide an indication of the degree of identity. In some embodiments, two sequences are considered to be substantially identical if at least 50%, 55%, 60%, 65%, 70%, 75%, 80%, 85%, 90%, 91%, 92%, 93%, 94%, 95%, 96%, 97%, 98%, 99% or more of their corresponding residues are identical over a relevant stretch of residues. In some embodiments, the relevant stretch is a complete sequence. In some embodiments, the relevant stretch is at least 10, 15, 20, 25, 30, 35, 40, 45, 50, or more residues.

The phrase "targeting vector" or "targeting construct" as used herein refers to a polynucleotide molecule that comprises a targeting region. A targeting region comprises a sequence that is identical or substantially identical to a sequence in a target cell, tissue or animal and provides for integration of the targeting construct into a position within the genome of the cell, tissue or animal via homologous recombination. Targeting regions that target using site-specific recombinase recognition sites (e.g., LoxP or Frt sites) are also included. In some embodiments, a targeting construct of the present invention further comprises a nucleic acid sequence or gene of particular interest, a selectable marker, control and or regulatory sequences, and other nucleic acid sequences that allow for recombination mediated through exogenous addition of proteins that aid in or facilitate recombination involving such sequences. In some embodiments, a targeting construct of the present invention further comprises a gene of interest in whole or in part, wherein the gene of interest is a heterologous gene that encodes a protein in whole or in part that has a similar function as a protein encoded by an endogenous sequence.

The term "variant", as used herein, refers to an entity that shows significant structural identity with a reference entity but differs structurally from the reference entity in the presence or level of one or more chemical moieties as compared with the reference entity. In many embodiments, a variant also differs functionally from its reference entity. In general, whether a particular entity is properly considered to be a "variant" of a reference entity is based on its degree of structural identity with the reference entity. As will be appreciated by those skilled in the art, any biological or chemical reference entity has certain characteristic structural elements. A variant, by definition, is a distinct chemical entity that shares one or more such characteristic structural elements. To give but a few examples, a small molecule may have a characteristic core structural element (e.g., a macrocycle core) and/or one or more characteristic pendent moieties so that a variant of the small molecule is one that shares the core structural element and the characteristic pendent moieties but differs in other pendent moieties and/or in types of bonds present (single vs. double, E vs. Z, etc.) within the core, a polypeptide may have a characteristic sequence element comprised of a plurality of amino acids having designated positions relative to one another in linear or three-dimensional space and/or contributing to a particular biological function, a nucleic acid may have a characteristic sequence element comprised of a plurality of nucleotide residues having designated positions relative to one another in linear or three-dimensional space. For example, a variant polypeptide may differ from a reference polypeptide as a result of one or more differences in amino acid sequence and/or one or more differences in chemical moieties (e.g., carbohydrates, lipids, etc.) covalently attached to the polypeptide backbone. In some embodiments, a variant polypeptide shows an overall sequence identity with a reference polypeptide that is at least 85%, 86%, 87%, 88%, 89%, 90%, 91%, 92%, 93%, 94%, 95%, 96%, 97%, or 99%. Alternatively or additionally, in some embodiments, a variant polypeptide does not share at least one characteristic sequence element with a reference polypeptide. In some embodiments, the reference polypeptide has one or more biological activities. In some embodiments, a variant polypeptide shares one or more of the biological activities of the reference polypeptide. In some embodiments, a variant polypeptide lacks one or more of the biological activities of the reference polypeptide. In some embodiments, a variant polypeptide shows a reduced level of one or more biological activities as compared with the reference polypeptide. In many embodiments, a polypeptide of interest is considered to be a "variant" of a parent or reference polypeptide if the polypeptide of interest has an amino acid sequence that is identical to that of the parent but for a small number of sequence alterations at particular positions. Typically, fewer than 200/%, 15%, 10%, 9%, 8%, 7%, 6%, 5%, 4%, 3%, 2% of the residues in the variant are substituted as compared with the parent. In some embodiments, a variant has 10, 9, 8, 7, 6, 5, 4, 3, 2, or 1 substituted residue as compared with a parent. Often, a variant has a very small number (e.g., fewer than 5, 4, 3, 2, or 1) number of substituted functional residues (i.e., residues that participate in a particular biological activity). Furthermore, a variant typically has not more than 5, 4, 3, 2, or 1 additions or deletions, and often has no additions or deletions, as compared with the parent. Moreover, any additions or deletions are typically fewer than about 25, about 20, about 19, about 18, about 17, about 16, about 15, about 14, about 13, about 10, about 9, about 8, about 7, about 6, and commonly are fewer than about 5, about 4, about 3, or about 2 residues. In some embodiments, the parent or reference polypeptide is one found in nature. As will be understood by those of ordinary skill in the art, a plurality of variants of a particular polypeptide of interest may commonly be found in nature, particularly when the polypeptide of interest is an infectious agent polypeptide.

The term "vector", as used herein, refers to a nucleic acid molecule capable of transporting another nucleic acid to which it is associated. In some embodiment, vectors are capable of extra-chromosomal replication and/or expression of nucleic acids to which they are linked in a host cell such as a eukaryotic and/or prokaryotic cell. Vectors capable of directing the expression of operatively linked genes are referred to herein as "expression vectors."

The term "wild-type", as used herein, has its art-understood meaning that refers to an entity having a structure and/or activity as found in nature in a "normal" (as contrasted with mutant, diseased, altered, etc.) state or context. Those of ordinary skill in the art will appreciate that wild type genes and polypeptides often exist in multiple different forms (e.g., alleles).

DETAILED DESCRIPTION OF CERTAIN EMBODIMENTS

The present invention provides, among other things, improved and/or engineered non-human animals having humanized genetic material encoding an a proliferation-inducing ligand protein (e.g., APRIL). In certain embodiments, such non-human animals are useful, for example, for assays in transplant engraftment, B cell activation and survival of antigen-specific B cells post immunization. It is contemplated that such non-human animals provide an improvement in B cell activation and survival of antigen-specific B cells post immunization post-engraftment of human hematopoietic stem cells. Therefore, the present invention is particularly useful for maintaining human hematopoietic cells in non-human animals. In particular, the present invention encompasses the humanization of a rodent April gene resulting in expression of a humanized protein on the plasma membrane surface of cells of the non-human animal. Such humanized proteins have the capacity to recognize engrafted human cells via engagement of humanized April proteins and ligands/receptors present on the surface of the engrafted human cells. In some embodiments, non-human animals of the present invention are capable of receiving transplanted human hematopoietic cells; in some embodiments, such non-human mammals develop and/or have an immune system comprising human cells. In some embodiments, humanized April proteins have sequence encoded by exons 2 to 6 of a human APRIL gene. In some embodiments, non-human animals of the present invention comprise a genetically modified April gene that contains genetic material from the non-human animal and a heterologous species (e.g., a human). In some embodiments, non-human animals of the present invention comprise a humanized April gene, wherein the humanized April gene comprises exons 2, 3, 4, 5 and 6 of a human APRIL gene. In some embodiments, the expression of the humanized April protein is under the control of non-human April genetic material (e.g., a non-human April gene promoter).

Various aspects of the invention are described in detail in the following sections. The use of sections is not meant to limit the invention. Each section can apply to any aspect of the invention. In this application, the use of "or" means "and/or" unless stated otherwise.

A Proliferation-Inducing Ligand (APRIL) Gene

A proliferation-inducing ligand (APRIL) is a member of the tumor necrosis factor (TNF) ligand superfamily and is expressed by many different cell types including, but not limited to dendritic cells, epithelial cells, macrophages, monocytes, osteoclasts and T cells. APRIL (also referred to as tumor necrosis factor ligand superfamily member 13, TNFSF 13, CD256, TALL-2, TALL2, TRDL-1 and ZTNF2) is expressed on the cell surface as a Type II transmembrane protein and can be released in soluble form via cleavage at a furin consensus site after proteolysis. The gene structure for APRIL in mouse and man are similar in that both genes contain 6 exons with the first two encoding the transmembrane portion and the remaining exons encoding the extracellular portion of the protein. Also, in both humans and mice, the furin cleavage site is encoded by exon 2. For both mouse and man, alternative splice variants have been reported. In humans, alternative splicing that combines exon 1 and 3 generates a membrane-bound form that is resistant to cleavage due to the absence of the furin cleavage site encoded by exon 2. This variant has been named APRIL-δ. Other alternative splice variants that skip exon 3 (APRIL-β) or splice a cryptic intron in exon 6 (APRIL-γ) have been reported. However, these splice variants have not been observed in mice. In contrast, splice variants that result in single amino differences at amino acid residue 120 have been reported and have only slight differences in binding to receptors.

The APRIL gene in both mouse and man is located 3' of another gene in the TNF ligand superfamily, TNF-related weak inducer of apoptosis (TWEAK). Notably, in both mouse and man a unique intergenic splicing event has been observed that yields a variant referred to as TWE-PRIL. In humans, this intergenic splicing occurs between exon 6 of TWEAK and exon 2 of APRIL, whereas in mice, the splicing is between exon 7 of TWEAK and exon 1 of APRIL. TWE-PRIL has been shown to stimulate both T and B cells in vitro and induce proliferation.

Reported receptors for APRIL include transmembrane activator and calcium modulator and cyclophilin ligand interactor (TACI) and B cell maturation antigen (BCMA). A related TNF family ligand (BAFF) also binds to TACI and BCMA, as well as a third receptor BAFF-R. BAFF binding to BAFF-R is unique to BAFF and not shared by APRIL.

The role of APRIL, in particular, has been investigated in respect of its role in the modulation of B and T cell responses. In particular, APRIL has been reported to stimulate the growth of tumor cells in vitro and in vivo. For example, Hahne et al. (1998, J. Exp. Med. 188(6):1185-1190) reported that soluble APRIL increased proliferation of tumor cells in culture in a dose dependent manner, and, when transfected as full-length into tumor cells, lead to a faster rate of proliferation than mock-treated or wild-type cells.

APRIL Sequences

Exemplary APRIL sequences for human and mouse are set forth in Table 3. For cDNA sequences, consecutive exons are separated by alternating underlined text.

TABLE 3

| Mouse April cDNA NM_001159505.1 | GAAGGCTGGCCGCTCCTTCTGGGTGTCACGGCTGCCCTGTCCTT CCTAGATAATGGCACCAAATTCTCCTGAGGCTAGGGGGGAAGGA GTGTCAGAGTGTCACTAGCTCGACCCTGGGGACAAGGGGGACTA ATAGTACCCTAGCTTGATTTCTTCCTATTCTCAAGTTCCTTTTT ATTTCTCCCTTGCGTAACCCGCTCTTCCCTTCTGTGCCTTTGCC TGTATTCCCACCCTCCCTGCTACCTCTTGGCCACCTCACTTCTG AGACCACAGCTGTTGGCAGGGTCCCTAGCTCATGCCAGCCTCAT CTCCAGGCCACATGGGGGGCTCAGTCAGAGAGCCAGCCCTTTCG GTTGCTCTTTGGTTGAGTTGGGGGGCAGTTCTGGGGGCTGTGAC TTGTGCTGTCGCACTACTGATCCAACAGACAGAGCTGCAAAGCC TAAGGCGGGAGGTGAGCCGGCTGCAGCGGAGTGGAGGGCCTTCC CAGAAGCAGGGAGAGCGCCCATGGCAGAGCCTCTGGG<u>AGCAGAG TCCTGATGTCCTGGAAGCCTGGAAGGATGGGGCGAAATCTCGGA GAAGGAGAGCAGTACTCACCCAGAAGCACAAGAAGAAGCACTCA GTCCTGCATCTTGTTCCAGTTAACATTACCTCCAAGG</u>ACTCTGA CGTGACAGAGGTGATGTGGCAACCAGTACTTAGGCGTGGGAGAG GCCTGGAGGCCCAGGGAGACATTGTACGAGTCTGGGACACTGGA ATTTATCTGCTCTATAGTCAGGTCCTGTTTCATGATGTGAGTTT CACAATGGGTCAGGTGGTATCTCGGGAAGGACAAGGGAGAAGAG AAACTCTATTCCGATGTATCAGAAGTATGCCTTCTGATCCTGAC CGTGCCTACAATAGCTGCTACAGTGCAGG<u>TGTCTTTCATTTACA TCAAGGGGATATTATCACTGTCAAAATTCCACGGGCAAACGCAA AACTTAGCCTTTCTCCGCATGGAACATTCCTGGGGTTTGTGAAA CTATGATTGTTATAAAGGGGGTGGGGATTTCCCATTCCAAAAAC TGGCTAGACAAAGGACAAGGAACGGTCAAGAACAGCTCTCCATG GCTTTGCCTTGACTGTTGTTCCTCCCTTTGCCTTTCCCGCTCCC ACTATCTGGGCTTTGACTCCATGGATATTAAAAAAGTAGAATAT TTTGTGTTTATCTCCCACACAGCCCCAAATTCTTTTGTTGTGTG TGCGAAGGGGGTTTTGCGCACTGTGCCAAGCCTTGTCCACTGGA ATGCATCCAGAACAGCAGCACCATCTAGCGGCAGGTTGAGGAAA GACTATGGTCTCTGCTAGGGAAAACCTTATCCAACTCTTCAAGT ACCCTCTGCTTCAATTAACAAGAAGCCCGGCTTTCAGTATTTCA CCTATTGCGTCCAAATTCTTGTTACTATCTAGAAAAAGATATAT GTTAGGTGCCTCGATATGCATGCCATTCATCCTCCCCATTCTCC</u> |

TABLE 3-continued

|  |  |
|---|---|
|  | TATACACTTCCGAGCTGGGCACTGAGCTTTACGCCTTAAATCAC<br>AGTACTCGGGAGGCAGATCTCGATGAGTTCGAGGCCAACTTGGT<br>CTAAATAGTGAGTTCCAGGCCACCCAGGGGTTACAATGGTGAGA<br>CCCTGTCTCAAACAAACTAACAAACAAATAAACGAAAGGCTCTC<br>CACG(SEQ ID NO: 1) |
| Mouse April Protein<br>NP_001152977.1 | MPASSPGHMGGSVREPALSVALWLSWGAVLGAVTCAVALLIQQT<br>ELQSLRREVSRLQRSGGPSQKQGERPWQSLWEQSPDVLEAWKDG<br>AKSRRRRAVLTQKHKKKHSVLHLVPVNITSKDSDVTEVMWQPVL<br>RRGRGLEAQGDIVRVWDTGIYLLYSQVLFHDVTFTMGQVVSREG<br>QGRRETLFRCIRSMPSDPDRAYNSCYSAGVFHLHQGDIITVKIP<br>RANAKLSLSPHGTFLGFVKL (SEQ ID NO: 2) |
| Mouse TWE-PRIL Protein<br>NP_001152975.1 | MAARRSQRRRGRRGEPGTALLAPLVLSLGLALACLGLLLVVVSL<br>GSWATLSAQEPSQEELTAEDRREPPELNPQTEESQDVVPFLEQL<br>VRPRRSAPKGRKARPRRAIAAHYEVHPRPGQDGAQAGVDGTVSG<br>WEETKINSSSPLRYDRQIGEFTVIRAGLYYLYCQVHFDEGKAVY<br>LKLDLLVNGVLALRCLEEFSATAASSPGPQLRLCQTELQSLRRE<br>VSRLQRSGGPSQKQGERPWQSLWEQSPDVLEAWKDGAKSRRRRA<br>VLTQKHKKKHSVLHLVPVNITSKDSDVTEVMWQPVLRRGRGLEA<br>QGDIVRVWDTGIYLLYSQVLFHDVTFTMGQVVSREGQGRRETLF<br>RCIRSMPSDPDRAYNSCYSAGVFHLHQGDIITVKIPRANAKLSL<br>SPHGTFLGFVKL (SEQ ID NO: 3) |
| Human APRIL cDNA<br>NM_003808.3 | CCGGAACCCTGTGTGCTGGGGAGGAATCCCGCAGTGGCCGGGGG<br>GCTTGAGGCCGCTGCTTTGTCTCTTCGTCCAGAGCCTTATGTAA<br>GAGCTTTTCTCGGGAAACAGGAAGTCCTGCTTGCCAATTTCAGC<br>ACAGGGAGTAGTGCAGGCCTTATTCCAACACACCCGGCCCAGCC<br>TTAACCCCAGAACTCAGCCAGTTTCTTGCTTCCGTGCCCCTGGT<br>TCTCCTCCCCATCGAGCCCACCCCTCCTTTCCCACCTTCAGTCA<br>CCCCTAGTGAACTGCCCCAGCGATCTCTGCTGTGCTTGAGCCCG<br>AGGGTCTTCCACCCTCGCCCTGACCCTGGACACTGCCCAGCTTG<br>GCCCCCCATCCTGCTCCTGGCACAATGCCCTCTAGCCAGCCAAC<br>CTTCCCTCCCCCAACCCTGGGGCCGCCCCAGGGTTCCTGCGCAC<br>TGCCTGTTCCTCCTGGGTGTCACTGGCAGCCCTGTCCTTCCTAG<br>AGGGACTGGAACCTAATTCTCCTGAGGCTGAGGGAGGGTGGAGG<br>GTCTCAAGGCAACGCTGGCCCCACGACGGAGTGCCAGGAGCACT<br>AACAGTACCCTTAGCTTGCTTTCCTCCTCCCTCCTTTTTATTTT<br>CAAGTTCCTTTTTATTTCTCCTTGCGTAACAACCTTCTTCCCTT<br>CTGCACCACTGCCCGTACCCTTACCCGCCCCGCCACCTCCTTGC<br>TACCCCACTCTTGAAACCACAGCTGTTGGCAGGGTCCCCAGCTC<br>ATGCCAGCCTCATCTCCTTTCTTGCTAGCCCCAAAGGGCCTCC<br>AGGCAACATGGGGGCCCAGTCAGAGAGCCGGCACTCTCAGTTG<br>CCCTCTGGTTGAGTTGGGGGGCAGCTCTGGGGGCCGTGGCTTGT<br>GCCATGGCTCTGCTGACCCAACAAACAGAGCTGCAGAGCCTCAG<br>GAGAGAGGTGAGCCGGCTGCAGGGGACAGGAGGCCCCTCCCAGA<br>ATGGGGAAGGGTATCCCTGGCAGAGTCTCCCGGAGCAG<u>AGTTCC<br>GATGCCCTGGAAGCCTGGGAGAATGGGGAGAGATCCCGGAAAAG<br>GAGAGCAGTGCTCACCCAAAAACAGAAGAAGCAGCACTCTGTCC<br>TGCACCTGGTTCCCATTAACGCCACCTCCAAGG</u>ATGACTCCGAT<br>GTGACAGAGGTGATGTGGCAACCAGCTCTTAGGCGTGGGAGAGG<br>CCTACAGGCCCAAGGATATGGTGTCCGAATCCAGGATGCTGGAG<br>TTTATCTGCTGTATAGCCAGGTCCTGTTTCAAGACGTGAGTTTC<br>ACCATGGGTCAGGTGGTGTCTCGAGAAGGCCAAGGAAGGCAGGA<br>GAGTCTATTCCGATGTATAAGAAGTATGCCCTCCCACCCGGACC<br>GGGCCTACAACAGCTGCTATAGCGCAGG<u>TGTCTTCCATTTACAC<br>CAAGGGGATATTCTGAGTGTCATAATTCCCGGGCAAGGGCGAA<br>ACTTAACCTCTCTCCACATGGAACCTTCCTGGGGTTTGTGAAAC<br>TGTGATTGTGTTATAAAAAGTGGCTCCCAGCTTGGAAGACCAGG<br>GTGGGTACATACTGGAGACAGCCAAGAGCTGAGTATATAAAGGA<br>GAGGGAATGTGCAGGAACAGAGGCGTCTTCCTGGGTTTGGCTCC<br>CCGTTCCTCACTTTTCCCTTTTCATTCCCACCCCCTAGACTTTG<br>ATTTTACGGATATCTTGCTTCTGTTCCCCATGGAGCTCCGAATT<br>CTTGCGTGTGTAGATGAGGGCGGGGACGGGCGCCAGGCAT<br>TGTCCAGACCTGGTCGGGGCCCACTGGAAGCATCCAGAACAGCA<br>CCACCATCTAGCGGCCGCTCGAGGGAAGCACCCGCCGGTTGGCC<br>GAAGTCCACGAAGCCGCCCTCTGCTAGGGAAAACCCCTGGTTCT<br>CCATGCCACACCTCTCTCCAGGTGCCCTCTGCCTCTTCACCCCA<br>CAAGAAGCCTTATCCTACGTCCTTCTCTCCATCTATCGGACCCC<br>AGTTTCCATCACTATCTCCAGAGATGTAGCTATTATGCGCCCGT<br>CTACAGGGGGTGCCCGACGATGACGGTGCCTTCGCAGTCAAATT<br>ACTCTTCGGGTCCCAAGGTTTGGCTTTCACGCGCTCCATTGCCC<br>CGGCGTGGCAGGCCATTCCAAGCCCTTCCGGGCTGGAACTGGTG<br>TCGGAGGAGCCTCGGGTGTATCGTACGCCCTGGTGTTGGTGTTG<br>CCTCACTCCTCTGAGCTCTTCTTTCTGATCAAGCCCTGCTTAAA<br>GTTAAATAAATAGAATGAATGATACCCCGGCAAAAAAAAAAA</u><br>AAAAA<br>(SEQ ID NO: 4) |

TABLE 3-continued

| | |
|---|---|
| Human APRIL Protein NP_003799.1 | MPASSPFLLAPKGPPGNMGGPVREPALSVALWLSWGAALGAVAC AMALLTQQTELQSLRREVSRLQGTGGPSQNGEGYPWQSLPEQSS DALEAWENGERSRKRRAVLTQKQKKQHSVLHLVPINATSKDDSD VTEVMWQPALRRGRGLQAQGYGVRIQDAGVYLLYSQVLFQDVTF TMGQVVSREGQGRQETLFRCIRSMPSHPDRAYNSCYSAGVFHLH QGDILSVIIPRARAKLNLSPHGTFLGFVKL (SEQ ID NO: 5) |
| Human APRIL-β Protein NP_742084.1 | MPASSPFLLAPKGPPGNMGGPVREPALSVALWLSWGAALGAVAC AMALLTQQTELQSLRREVSRLQGTGGPSQNGEGYPWQSLPEQSS DALEAWENGERSRKRRAVLTQKQKNDSDVTEVMWQPALRRGRGL QAQGYGVRIQDAGVYLLYSQVLFQDVTFTMGQVVSREGQGRQET LFRCIRSMPSHPDRAYNSCYSAGVFHLHQGDILSVIIPRARAKL NLSPHGTFLGFVKL (SEQ ID NO: 6) |
| Human APRIL-γ Protein NP_742085.1 | MPASSPFLLAPKGPPGNMGGPVREPALSVALWLSWGAALGAVAC AMALLTQQTELQSLRREVSRLQGTGGPSQNGEGYPWQSLPEQSS DALEAWENGERSRKRRAVLTQKQKKQHSVLHLVPINATSKDDSD VTEVMWQPALRRGRGLQAQGYGVRIQDAGVYLLYSQVLFQDVTF TMGQVVSREGQGRQETLFRCIRSMPSHPDRAYNSCYSAGVFHLH QGDILSVIIPRARAKLNLSPHGTFLGL (SEQ ID NO: 7) |
| Human APRIL-δ Protein NP_001185551.1 | MPASSPFLLAPKGPPGNMGGPVREPALSVALWLSWGAALGAVAC AMALLTQQTELQSLRREVSRLQGTGGPSQNGEGYPWQSLPEQQH SVLHLVPINATSKDDSDVTEVMWQPALRRGRGLQAQGYGVRIQD AGVYLLYSQVLFQDVTFTMGQVVSREGQGRQETLFRCIRSMPSH PDRAYNSCYSAGVFHLHQGDILSVIIPRARAKLNLSPHGTFLGF VKL (SEQ ID NO: 8) |
| Human APRIL-ζ Protein NP_001185552.1 | MPASSPFLLAPKGPPGNMGGPVREPALSVALWLSWGAALGAVAC AMALLTQQTELQSLRREVSRLQGTGGPSQNGEGYPWQSLPEQHS VLHLVPINATSKDDSDVTEVMWQPALRRGRGLQAQGYGVRIQDA GVYLLYSQVLFQDVTFTMGQVVSREGQGRQETLFRCIRSMPSHP DRAYNSCYSAGVFHLHQGDILSVIIPRARAKLNLSPHGTFLGFV KL (SEQ ID NO: 9) |
| Human APRIL-η Protein NP_001185553.1 | MGGPVREPALSVALWLSWGAALGAVACAMALLTQQTELQSLRRE VSRLQGTGGPSQNGEGYPWQSLPEQHSVLHLVPINATSKDDSDV TEVMWQPALRRGRGLQAQGYGVRIQDAGVYLLYSQVLFQDVTFT MGQVVSREGQGRQETLFRCIRSMPSHPDRAYNSCYSAGVFHLHQ GDILSVIIPRARAKLNLSPHGTFLGFVKL (SEQ ID NO: 10) |
| Human TWE-PRIL Protein NP_742086.1 | MAARRSQRRRGRRGEPGTALLVPLALGLGLALACLGLLLAVVSL GSRASLSAQEPAQEELVAEEDQDPSELNPQTEESQDPAPFLNRL VRPRRSAPKGRKTRARRAIAAHYEVHPRPGQDGAQAGVDGTVSG WEEARINSSSPLRYNRQIGEFIVTRAGLYYLYCQSSDALEAWEN GERSRKRRAVLTQKQKKQHSVLHLVPINATSKDDSDVTEVMWQP ALRRGRGLQAQGYGVRIQDAGVYLLYSQVLFQDVTFTMGQVVSR EGQGRQETLFRCIRSMPSHPDRAYNSCYSAGVFHLHQGDILSVI IPRARAKLNLSPHGTFLGFVKL (SEQ ID NO: 11) |
| Humanized April Protein | MPASSPGHMGGSVREPALSVALWLSWGAVLGAVTCAVALLIQQT ELQSLRREVSRLQRSGGPSQKQGERPWQSLWEQ*SSDALEAWENG ERSRKRRAVLTQKQKKQHSVLHLVPINATSKDDSDVTEVMWQPA LRRGRGLQAQGYGVRIQDAGVYLLYSQVLFQDVTFTMGQVVSRE GQGRQETLFRCIRSMPSHPDRAYNSCYSAGVFHLHQGDILSVII PRARAKLNLSPHGTFLGFVKL* (SEQ ID NO: 12) |

Humanized April Non-Human Animals

Non-human animals are provided that express humanized April proteins on the surface of cells (e.g., dendritic cells) of the non-human animals. Specifically, the present invention provides non-human animals that express humanized April proteins on the surface of their cells, the proteins being encoded by and/or expressed from a genetic modification of an endogenous locus of the non-human animal that encodes an April protein. Suitable examples presented herein specifically exemplify rodents, in particular, mice.

A genetically modified April gene, in some embodiments, comprises genetic material from a heterologous species (e.g., humans), wherein the genetically modified April gene encodes a April protein that comprises the encoded portion of the genetic material from the heterologous species. In some embodiments, a genetically modified APRIL gene of the present invention comprises genomic DNA of a heterologous species that corresponds to the extracellular portion of a April protein that is expressed on the plasma membrane of a cell. Non-human animals, embryos, cells and targeting constructs for making non-human animals, non-human embryos, and cells containing said genetically modified April gene are also provided.

In some embodiments, an endogenous April gene is deleted. In some embodiments, an endogenous April gene is altered, wherein a portion of an endogenous April gene is replaced with a heterologous sequence (e.g., a human APRIL gene sequence, in whole or in part). In some embodiments, all or substantially all of the endogenous April gene is replaced with a heterologous gene (e.g., a human APRIL gene). In some embodiments, a portion of a heterologous APRIL gene is inserted into an endogenous non-human April gene. In some embodiments, the heterologous gene is a human gene.

A non-human animal of the present invention contains a human APRIL gene, in whole or in part, at an endogenous non-human April locus. Thus, such non-human animals can be described as having a humanized April gene. The replaced, inserted or modified endogenous April gene (i.e., the humanized April gene) can be detected using a variety of methods including, for example, PCR, Western blot, Southern blot, restriction fragment length polymorphism (RFLP), or a gain or loss of allele assay.

In various embodiments, a humanized April gene according to the present invention includes a April gene that has a second, third, fourth, fifth, and sixth exon each having a sequence at least 50% (e.g., 50%, 55%, 60%, 65%, 70%, 75%, 80%, 85%, 90%, 91%, 92%, 93%, 94%, 95%, 96%, 97%, 98%, 99% or more) identical to a second, third, fourth, fifth, and sixth exon that appear in a human APRIL gene of Table 3.

In various embodiments, a humanized April gene according to the present invention includes a April gene that has a nucleotide coding sequence (e.g., a cDNA sequence) at least 50% (e.g., 50%, 55%, 600/%, 65%, 70%, 75%, 80%, 85%, 90%, 91%, 92%, 93%, 94%, 95%, 96%, 97%, 98%, 99% or more) identical to nucleotides 1007-2276 that appear in a human APRIL cDNA sequence of Table 3.

In various embodiments, a humanized April protein produced by a non-human animal of the present invention has an extracellular portion having a sequence that is at least 50% (e.g., 50%, 55%, 60%, 65%, 70%, 75%, 80%, 85%, 90%, 91%, 92%, 93%, 94%, 95%, 96%, 97%, 98%, 99% or more) identical to an extracellular portion of a human APRIL protein that appears in Table 3.

In various embodiments, a humanized April protein produced by a non-human animal of the present invention has an extracellular portion having a sequence that is at least 50% (e.g., 50%, 55%, 60%, 65%, 70%, 75%, 80%, 85%, 90%, 91%, 92%, 93%, 94%, 95%, 96%, 97%, 98%, 99% or more) identical to amino acid residues 87 to 250 that appear in a human APRIL protein of Table 3.

In various embodiments, a humanized April protein produced by a non-human animal of the present invention has an amino acid sequence that is at least 50% (e.g., 50%, 55%, 60%, 65%, 70%, 75%, 80%, 85%, 90%, 91%, 92%, 93%, 94%, 95%, 96%, 97%, 98%, 99% or more) identical to an amino acid sequence of a humanized APRIL protein that appears in Table 3.

In various embodiments, a humanized April protein produced by a non-human animal of the present invention has an amino acid sequence that is at least 50% (e.g., 50%, 55%, 60%, 65%, 70%, 75%, 80%, 85%, 90%, 91%, 92%, 93%, 94%, 95%, 96%, 97%, 98%, 99% or more) identical to an amino acid sequence of a human APRIL protein that appears in Table 3.

Compositions and methods for making non-human animals that expresses a humanized April protein, including specific polymorphic forms or allelic variants (e.g., single amino acid differences, alternative splice variants, etc.), are provided, including compositions and methods for making non-human animals that expresses such proteins from a human promoter and a human regulatory sequence or, optionally, from a non-human promoter and a non-human regulatory sequence. In some embodiments, compositions and methods for making non-human animals that expresses such proteins from an endogenous promoter and an endogenous regulatory sequence are also provided. The methods include inserting the genetic material encoding a human APRIL protein, in whole or in part, at a precise location in the genome of a non-human animal that corresponds to an endogenous April gene thereby creating a humanized April gene that expresses an April protein that is human, in whole or in part. In some embodiments, the methods include inserting genomic DNA corresponding to exons 2 to 6 of a human APRIL gene into an endogenous April gene of the non-human animal thereby creating a humanized gene that encodes an APRIL protein that contains a human portion containing amino acids encoded by the inserted exons.

A humanized April gene approach employs a relatively minimal modification of the endogenous gene and results in natural APRIL-mediated signal transduction in the non-human animal, in various embodiments, because the genomic sequence of the APRIL gene is modified in a single fragment and therefore retain normal functionality by including necessary regulatory sequences. Thus, in such embodiments, the April gene modification does not affect other surrounding genes or other endogenous April genes. Further, in various embodiments, the modification does not affect the assembly of a functional transmembrane protein on the plasma membrane and maintains normal association with its receptors via binding and interaction of the extracellular portion with a given receptor which is unaffected by the modification.

A schematic illustration (not to scale) of endogenous murine and human APRIL genes is provided in FIG. 1. A schematic illustration (not to scale) of a humanized April gene is provided in FIG. 2B. As illustrated, genomic DNA containing exons 2 to 6 of a human APRIL gene is inserted into an endogenous murine April gene by a targeting construct. This genomic DNA comprises the portion of the gene that encodes the extracellular portion (e.g., amino acid residues 87 to 250) of a human APRIL protein responsible for receptor binding.

Figure 2A:
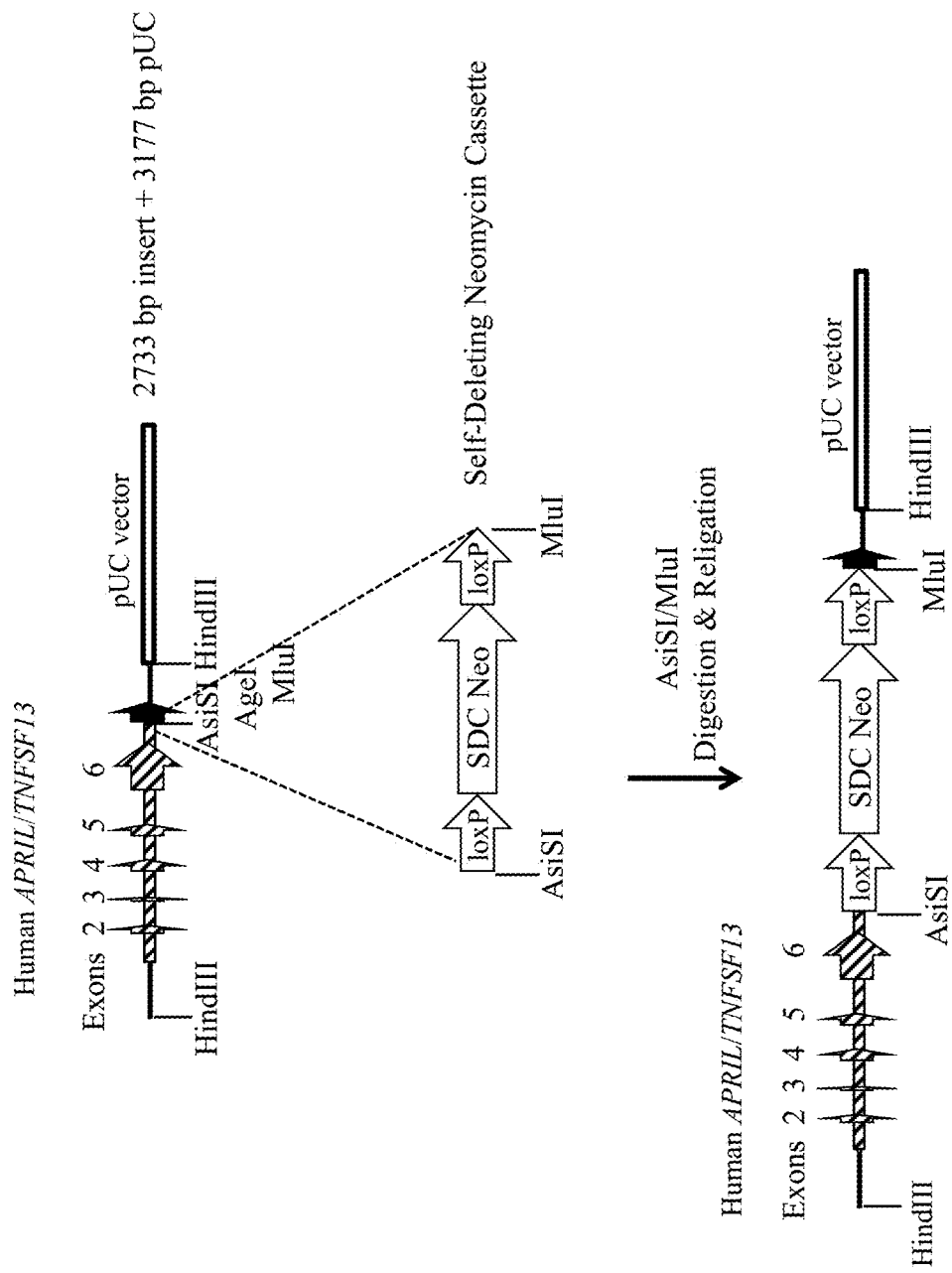
FIGS. 2A and 2B show diagrams, not to scale, of an exemplary method for making a targeting vector for humanization of a non-human A PRoliferation-Inducing Ligand (April) gene. Non-human sequences are shown as closed, black symbols. Human sequences are shown in open, diagonal filled symbols. SDC Neo: self-deleting neomycin selection cassette. LoxP: Cre recognition target site sequence. CM: chloramphenicol selection cassette. Restriction enzyme recognition sites are indicated (e.g., AsiSI, MluI, HindIII, etc.).
Figure 2B:
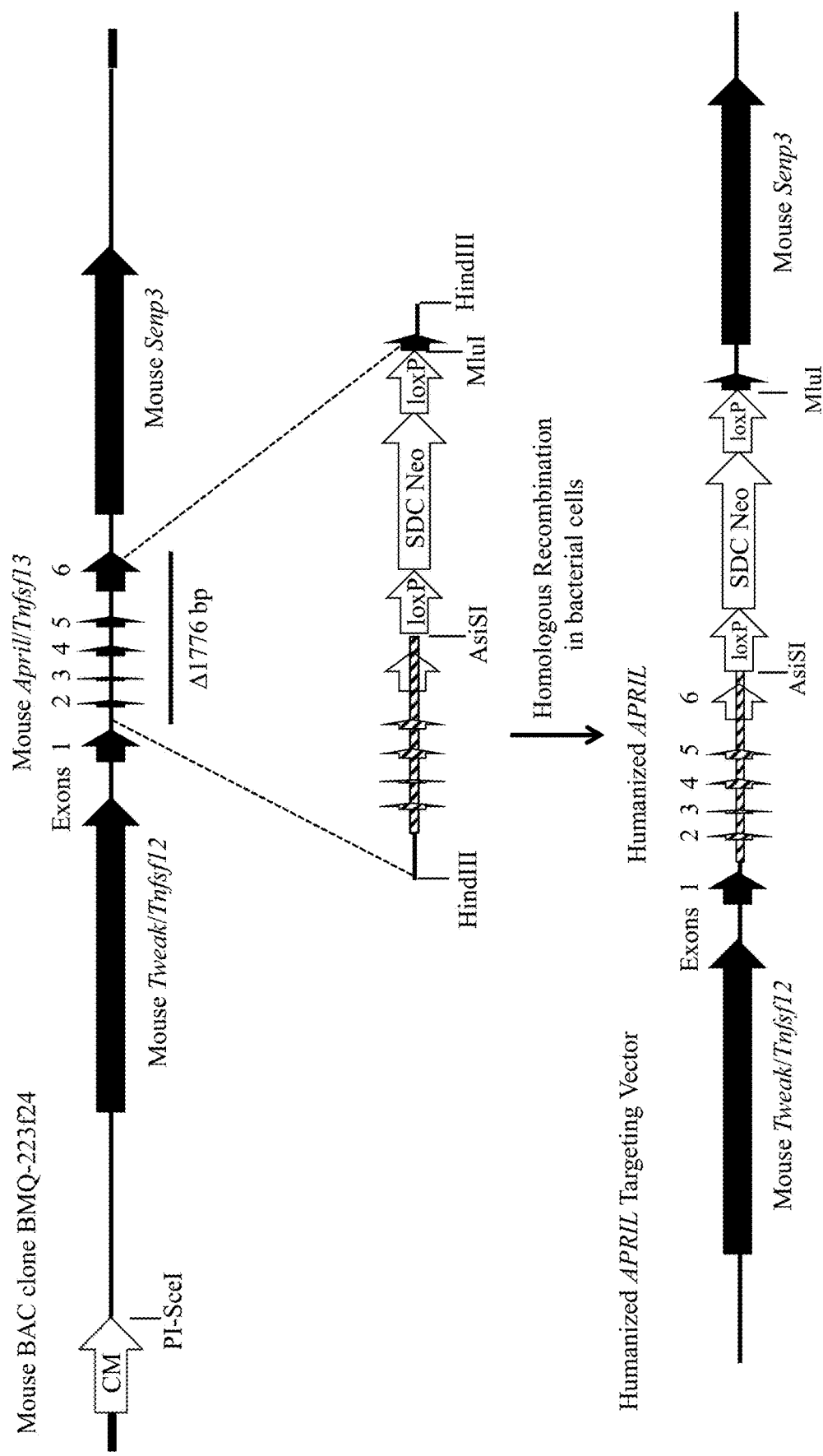

A non-human animal (e.g., a mouse) having a humanized April gene can be made by any method known in the art. For example, a targeting vector can be made that introduces a human APRIL gene, in whole or in part, with a selectable marker gene. FIG. 2A illustrates the initial steps of the construction of an exemplary targeting vector comprising exons 2 to 6 of a human APRIL gene and a self-deleting neomycin cassette (e.g., a neomycin resistance gene flanked on both sides by LoxP sequences; see U.S. Pat. Nos. 8,354,389 and 8,518,392, both of which are herein incorporated by reference) positioned 3' of the human exons. FIG. 2B illustrates a mouse genome comprising an insertion of exons 2 to 6 of a human APRIL gene using an exemplary targeting vector described in FIG. 2A. As illustrated, the targeting construct contains unique 5' and 3' regions of homology which allow for the precise insertion of the human genetic material comprising exons 2 to 6 of a human APRIL gene by homologous recombination. The targeting construct also contains a self-deleting drug selection cassette, which is positioned 3' of the genetic material comprising exons 2 to 6 of a human APRIL gene. Upon homologous recombination, exons 2 to 6 of a human APRIL gene are inserted into an endogenous murine April gene that has been specifically engineered to accept the human sequence contained in the targeting vector. A humanized April gene is created resulting in a cell or non-human animal that expresses a humanized April protein that contains amino acids encoded by exons 2 to 6 of a human APRIL gene. The drug selection cassette will be removed in a development-dependent manner, i.e., progeny derived from mice whose germ line cells containing the humanized April gene described above will shed the selectable marker from differentiated cells during development.

The non-human animals of the present invention may be prepared as described above, or using methods known in the art, to comprise additional human or humanized genes, oftentimes depending on the intended use of the non-human animal. Genetic material of such additional human or humanized genes may be introduced through the further alteration of the genome of cells (e.g., embryonic stem cells) having the genetic modifications as described above or through breeding techniques known in the art with other genetically modified strains as desired. In some embodiments, non-human animals of the present invention are prepared to further comprise one or more human or humanized genes selected from BAFF-R, TACI, and BCMA. In some embodiments, non-human animals of the present invention are prepared to further comprise a human or humanized B cell activating factor (BAFF) gene. In some embodiments, non-human animals of the present invention are prepared to further comprise a human or humanized TNF-related weak inducer of apoptosis (TWEAK). In some embodiments, non-human animals of the present invention comprise a humanized April gene as described herein and genetic material from a heterologous species (e.g., humans), wherein the genetic material encodes, in whole or in part, one or more heterologous proteins selected from BAFF-R, TACI, BCMA, BAFF and TWEAK.

In addition to mice having humanized April genes as described herein, also provided herein are other genetically modified non-human animals that comprise humanized APRIL genes. In some embodiments, such non-human animals comprise a humanized April gene operably linked to an endogenous April promoter sequence. In some embodiments, such non-human animals express a humanized April protein from an endogenous April locus, wherein the humanized April protein comprises amino acid residues 87 to 250 of a human APRIL protein.

Such non-human animals may be selected from the group consisting of a mouse, rat, rabbit, pig, bovine (e.g., cow, bull, buffalo), deer, sheep, goat, chicken, cat, dog, ferret, primate (e.g., marmoset, rhesus monkey). For the non-human animals where suitable genetically modifiable ES cells are not readily available, other methods are employed to make a non-human animal comprising the genetic modifications as described herein. Such methods include, e.g., modifying a non-ES cell genome (e.g., a fibroblast or an induced pluripotent cell) and employing nuclear transfer to transfer the modified genome to a suitable cell, e.g., an oocyte, and gestating the modified cell (e.g., the modified oocyte) in a non-human animal under suitable conditions to form an embryo.

In some embodiments, a non-human animal of the present invention is a mammal. In some embodiments, a non-human animal of the present invention is a small mammal, e.g., of the superfamily Dipodoidea or Muroidea. In some embodiments, a genetically modified animal of the present invention is a rodent. In some embodiments, a rodent of the present invention is selected from a mouse, a rat, and a hamster. In some embodiments, a rodent of the present invention is selected from the superfamily Muroidea. In some embodiments, a genetically modified animal of the present invention is from a family selected from Calomyscidae (e.g., mouse-like hamsters), Cricetidae (e.g., hamster, New World rats and mice, voles), Muridae (true mice and rats, gerbils, spiny mice, crested rats), Nesomyidae (climbing mice, rock mice, with-tailed rats, Malagasy rats and mice), Platacanthomyidae (e.g., spiny dormice), and Spalacidae (e.g., mole rats, bamboo rats, and zokors). In some certain embodiments, a genetically modified rodent of the present invention is selected from a true mouse or rat (family Muridae), a gerbil, a spiny mouse, and a crested rat. In some certain embodiments, a genetically modified mouse of the present invention is from a member of the family Muridae. In some embodiment, an non-human animal of the present invention is a rodent. In some certain embodiments, a rodent of the present invention is selected from a mouse and a rat. In some embodiments, a non-human animal of the present invention is a mouse.

In some embodiments, a non-human animal of the present invention is a rodent that is a mouse of a C57BL strain selected from C57BL/A, C57BL/An, C57BL/GrFa, C57BL/KaLwN, C57BL/6, C57BL/6J, C57BL/6ByJ, C57BL/6NJ, C57BL/10, C57BL/10ScSn, C57BL/10Cr, and C57BL/O1a. In some certain embodiments, a mouse of the present invention is a 129 strain selected from the group consisting of a strain that is 129P1, 129P2, 129P3, 129X1, 129S1 (e.g., 129S1/SV, 129S1/SvIm), 129S2, 129S4, 129S5, 129S9/SvEvH, 129/SvJae, 129S6 (129/SvEvTac), 129S7, 129S8, 129T1, 129T2 (see, e.g., Festing et al., 1999, Mammalian Genome 10:836; Auerbach et al., 2000, Biotechniques 29(5):1024-1028, 1030, 1032). In some certain embodiments, a genetically modified mouse of the present invention is a mix of an aforementioned 129 strain and an aforementioned C57BL/6 strain. In some certain embodiments, a mouse of the present invention is a mix of aforementioned 129 strains, or a mix of aforementioned BL/6 strains. In some certain embodiments, a 129 strain of the mix as described herein is a 129S6 (129/SvEvTac) strain. In some embodiments, a mouse of the present invention is a BALB strain, e.g., BALB/c strain. In some embodiments, a mouse of the present invention is a mix of a BALB strain and another aforementioned strain.

In some embodiments, a non-human animal of the present invention is a rat. In some certain embodiments, a rat of the present invention is selected from a Wistar rat, an LEA strain, a Sprague Dawley strain, a Fischer strain, F344, F6, and Dark Agouti. In some certain embodiments, a rat strain as described herein is a mix of two or more strains selected from the group consisting of Wistar, LEA, Sprague Dawley, Fischer, F344, F6, and Dark Agouti.

Methods Employing Non-Human Animals Having Humanized APRIL Genes

April transgenic and knock-out non-human animals (e.g., mice) have been reported (Stein et al., 2002, J. Clin. Invest., 109(12):1587-1598; Castigli et al., 2004, Proc. Nat. Acad. Sci., 101(11):3903-3908; Xiao et al., 2008, Eur. J. Immunol., 38(12):3450-3458). Such animals have been employed in a variety of assays to determine the molecular aspects of APRIL expression, function and regulation. However, they are not without limitation. For example, use of April transgenic mice have been limited due to specific expression patterns of the transgene, which can reasonably be attributed to construct design. Moreover, in such transgenic mice, detectable April expression was observed for only two of four transgenic lines, but only in T cells and no other cell type. Transgenic mice that express human APRIL has yielded results that conflict with previous studies. For example, mice that received several injections of recombinant human APRIL demonstrated complete activation of T cells, whereas transgenic mice expressing human APRIL failed to do the same. While April transgenic mice have proved useful in elucidating some APRIL-mediated biological function, they have demonstrated variability in the results obtained, which are based, at least in part, from the different approaches employed to make them. Therefore, current in vivo systems exploiting APRIL-mediated biology are incomplete. The full potential of the molecular aspects of APRIL-mediated biological function and signaling pathways has not been exploited in transgenic mice.

Non-human animals of the present invention provide an improved in vivo system and source of biological materials (e.g., cells) expressing human APRIL that are useful for a variety of assays. In various embodiments, non-human animals of the present invention are used to develop therapeutics that target human APRIL and/or modulate APRIL-mediated signaling pathways. In various embodiments, mice of the present invention are used to screen and develop candidate therapeutics (e.g., antibodies) that bind to human APRIL. In various embodiments, non-human animals of the present invention are used to determine the binding profile of antagonists and/or agonists a humanized APRIL on the surface of a cell of a non-human animal as described herein.

In various embodiments, non-human animals of the present invention are used to measure the therapeutic effect of blocking or modulating human APRIL signal transduction (e.g., phosphorylation) and the effect on gene expression as a result of cellular changes. In various embodiments, non-human animals of the present invention are used to measure the therapeutic effect of blocking or modulating human APRIL-TACI and/or APRIL-BCMA signaling pathways, for example, the modulation of NF-κB-mediated transcription of DNA. In various embodiments, a non-human animal of the present invention or cells isolated therefrom are exposed to a candidate therapeutic that binds to a human APRIL protein on the surface of a cell of the non-human animal and, after a subsequent period of time, analyzed for effects on APRIL-dependent processes, for example, stimulation of B and T cells, stimulation of tumor growth, long-term survival of antigen-specific B cells (e.g., plasma cells), and NF-κB activation.

Non-human animals of the present invention express humanized April protein, thus cells, cell lines, and cell cultures can be generated to serve as a source of humanized April for use in binding and functional assays, e.g., to assay for binding or function of a APRIL antagonist or agonist, particularly where the antagonist or agonist is specific for a human APRIL protein or epitope. In various embodiments, a humanized April protein expressed by a non-human animal as described herein may comprise a variant amino acid sequence. Variant human APRIL proteins having variations associated with ligand binding residues have been reported. In various embodiments, non-human animals of the present invention express a humanized April protein variant. In various embodiments, the variant is polymorphic at an amino acid position associated with ligand binding. In various embodiments, non-human animals of the present invention are used to determine the effect of ligand binding through interaction with a polymorphic variant of human APRIL. In some embodiments, non-human animals of the present invention express an alternative splice variant of human APRIL. In some certain embodiments, non-human animals of the present invention express a human APRIL splice variant protein that appears in Table 3.

Cells from non-human animals of the present invention can be isolated and used on an ad hoc basis, or can be maintained in culture for many generations. For example, cells from non-human animals of the present invention can be used in a variety of cellular assays known in the art. In various embodiments, cells from a non-human animal of the present invention are immortalized and maintained in culture indefinitely (e.g., in serial cultures).

In various embodiments, cells and/or non-human animals of the present invention are used in a survival and/or proliferation assay (e.g., employing B or T cells) to screen and develop candidate therapeutics that modulate human APRIL. Survival of auto-reactive B cells plays an important role in the chronic pathology of autoimmune diseases, such as, for example, systemic lupus erythematosus (SLE), therefore, candidate APRIL modulators (e.g., antagonists) may be identified, characterized and developed using cells of non-human animals of the present invention and/or a non-human animal as described herein. In some embodiments, cells and/or non-human animals of the present invention are used in a survival assay to determine the number of antigen-specific plasma B cells in the presence and absence of APRIL.

In various embodiments, cells and/or non-human animals of the present invention are used in various immunization regimens to determine the APRIL-mediated functions in the immune response to an antigen. In some embodiments, candidate therapeutics that bind to, or block one or more functions of, human APRIL are characterized in a non-human animal of the present invention. Suitable measurements include various cellular assays, proliferation assays, serum immunoglobulin analysis (e.g., antibody titer), cytotoxicity assays, characterization of ligand-receptor interactions (immunoprecipitation assays). In some embodiments, non-human animals of the present invention are used to characterize the APRIL-mediated functions regulating an immune response to an antigen. In some embodiments, the antigen is associated with an autoimmune disease or condition. In some embodiments, the antigen is a test antigen (e.g., ovalbumin or OVA). In some embodiments, the antigen is a target associated with a disease or condition suffered by one or more human patients in need of treatment.

In various embodiments, non-human animals of the present invention are used in serum assays for determining titers of double-stranded DNA (dsDNA) autoantibody production for testing the pharmaco-toxicological aspects of candidate therapeutics that target human APRIL. In some embodiments, double-stranded DNA (dsDNA) autoantibody production in non-human animals of the present invention results from one or more autoimmune diseases or conditions induced in the non-human animal.

In various embodiments, cells and/or non-human animals of the present invention are used to characterize the repertoire and/or specificity of antibodies generated in an immune response to antigen. In some embodiments, the immune response is characterized by the generation of autoantibodies that are specific for one or more tissues of a non-human animal of the present invention. In some embodiments, the therapeutic potential of compounds or biological agents to modulate APRIL-dependent regulation of the B cell repertoire is characterized and/or developed in in a non-human animal of the present invention.

In various embodiments, non-human animals of the present invention are used for challenge with one or more antigens to determine the therapeutic potential of compounds or biological agents to modulate APRIL-dependent regulation of an immune response, including but not limited to, the specific T cell-dependent and B cell-dependent responses to a given antigen.

In various embodiments, non-human animals of the present invention are used in transplantation or adoptive transfer experiments to determine the therapeutic potential of compounds or biological agents to modulate APRIL-dependent regulation of new lymphocytes and their immune function. In various embodiments, non-human animals of the present invention are transplanted with human B cells.

In various embodiments, cells of non-human animals of the present invention are used in T cell assays to determine the therapeutic potential of compounds or biological agents to modulate APRIL-dependent regulation of T cell-dependent response and function. Exemplary T cell assays include, but are not limited to, ELISpot, intracellular cytokine staining, major histocompatibility complex (MHC) restriction, viral suppression assays, cytotoxicity assays, proliferation assays and regulatory T cell suppression assays.

In various embodiments, cells of non-human animals of the present invention are used in tumor cell growth assays to determine the therapeutic potential of compounds or biological agents to modulate APRIL-dependent regulation and/or stimulation of tumor cell growth.

In various embodiments, an autoimmune disease or condition is induced in one or non-human animals of the present invention to provide an in vivo system for determining the therapeutic potential of compounds or biological agents to modulate APRIL-dependent regulation of one or more functions of the autoimmune disease or condition. In some embodiments, the autoimmune condition is an inflammatory condition, for example, arthritis (e.g., collagen-induced arthritis, CIA).

Non-human animals of the present invention provide an in vivo system for the analysis and testing of a drug or vaccine. In various embodiments, a candidate drug or vaccine may be delivered to one or more non-human animals of the present invention, followed by monitoring of the non-human animals to determine one or more of the immune response to the drug or vaccine, the safety profile of the drug or vaccine, or the effect on a disease or condition. Exemplary methods used to determine the safety profile include measurements of toxicity, optimal dose concentration, efficacy of the drug or vaccine, and possible risk factors. Such drugs or vaccines may be improved and/or developed in such non-human animals.

Non-human animals of the present invention provide an improved in vivo system for the development and characterization of candidate therapeutics for use in cancer. In various embodiments, non-human animals of the present invention may be implanted with a tumor, followed by administration of a candidate therapeutic. The tumor may be allowed sufficient time to be established in one or more locations within the non-human animal. Tumor cell proliferation, growth, etc. may be measured both before and after administration with the candidate therapeutic. Cytotoxicity of candidate therapeutics may also be measured in the non-human animal as desired.

Non-human animals of the present invention provide an improved in vivo system elucidating mechanisms of human cell-to-cell interaction through adoptive transfer. In various embodiments, non-human animals of the present invention may by implanted with a tumor xenograft, followed by a second implantation of tumor infiltrating lymphocytes in the non-human animals by adoptive transfer to determine the effectiveness in eradication of solid tumors or other malignancies. Such experiments may be done with human cells (e.g., B cell lymphomas) due to the exclusive presence of human APRIL without competition with endogenous APRIL of the non-human animal. Further, therapies and pharmaceuticals for use in xenotransplantation can be improved and/or developed in such non-human animals.

Non-human animals of the present invention provide an improved in vivo system for maintenance and development of human hematopoietic stem cells through engraftment. In various embodiments, non-human animals of the present invention provide improved development and maintenance of human stem cells within the non-human animal. In various embodiments, increased populations of differentiated human B and T cells are observed in the blood, bone marrow, spleen and thymus of the non-human animal. In various embodiments, non-human animals of the present invention provide an increase in the level of engraftment of human hematopoietic stem cells as compared to non-human animals that express both endogenous non-human and heterologous (e.g., human) APRIL.

Non-human animals of the present invention provide an improved in vivo system for maintenance and development of human B cells (e.g., from human donors) through engraftment. In various embodiments, non-human animals of the present invention provide improved development and maintenance of human B cells within the non-human animal. In various embodiments, increased populations of differentiated human B cells post-immunization are observed in one or more of the blood, bone marrow, spleen or a lymph node of the non-human animal. In various embodiments, non-human animals of the present invention provide an increase in the level of engraftment of human B cells as compared to non-human animals that express endogenous non-human April.

EXAMPLES

The following examples are provided so as to describe to those of ordinary skill in the art how to make and use methods and compositions of the invention, and are not intended to limit the scope of what the inventors regard as their invention. Unless indicated otherwise, temperature is indicated in Celsius, and pressure is at or near atmospheric.

Example 1. Humanization of an Endogenous Non-Human A PRoliferation-Inducing Ligand (April) Gene This example illustrates exemplary methods of humanizing an endogenous gene encoding A PRoliferation-Inducing Ligand (April) in a non-human animal such as a rodent (e.g., a mouse). Human APRIL is known to exist in several variant (or allelic) forms. The methods described in this example can be employed to humanize an endogenous April gene of a non-human animal using any human variant (or allele), or combination of human variants (or alleles or fragments thereof) as desired. In this example, a human APRIL, gene that appears in the human genome assembly (GRCh37) is employed for humanizing an endogenous April gene of a mouse.

A targeting vector for humanization of an extracellular region of a April gene was constructed using bacterial homologous recombination and VELOCIGENE® technology (see, e.g., U.S. Pat. No. 6,586,251 and Valenzuela et al., High-throughput engineering of the mouse genome coupled with high-resolution expression analysis, 2003, Nature Biotech. 21(6):652-659). An exemplary process for humanization of an endogenous April gene of a mouse is set forth in FIGS. 2A and 2B.

Briefly, a ~2293 bp DNA fragment containing exons 2 to 6 of a human APRIL gene was made by de novo DNA synthesis (Blue Heron Biotech). A unique polylinker, which contained AsiSI, AgeI, and MluI restriction recognition sites, was engineered at the 3' end of the human APRIL gene sequence. The DNA fragment also included 5' and 3' flanking mouse sequences corresponding intron 1 and the 3' UTR of a mouse April gene, respectively. Separately, a self-deleting neomycin cassette flanked by recombinase recognition sites (e.g., LoxP; see U.S. Pat. Nos. 8,354,389 and 8,518,392, both of which are herein incorporated by reference) from a plasmid pFHa0019 was engineered to contain unique AsiSI and MluI restriction sites at the 5' and 3' ends of the cassette, respectively. The DNA fragment containing exons 2 to 6 of a human APRIL gene flanked by mouse April gene sequences and the self-deleting neomycin cassette were separately digested with AsiSI and MluI to produce compatible cohesive fragments. The fragments were ligated together to insert the self-deleting cassette between the human APRIL exon 6 and the 3' flanking mouse sequence containing part of the 3' UTR of a mouse April gene. Positive bacterial clones were selected on ampicillin (from the pUC vector) and neomycin (SDC). The correctly ligated fragments were confirmed by PCR and restriction mapping.

Separately, a mouse BAC clone BMQ-223f24 (Invitrogen) was modified specifically to insert the engineered DNA fragment containing exons 2 to 6 of a human APRIL gene described above by homologous recombination in bacterial cells. The DNA fragment containing exons 2 to 6 of a human APRIL gene was linearized by digestion with HindIII. The linearized fragment was then used to replace the corresponding mouse sequence in BAC clone BMQ-223f24 by homologous recombination in bacterial cells. Positive clones containing a ~1776 bp deletion of mouse April exons 2 to 6 were selected using chloroamphenicol and neomycin. The final targeting vector contained, from 5' to 3', mouse genomic sequence including a mouse Tweak (Tnfsf12) gene and sequence 5' of a mouse April gene, a mouse April exon 1, ~100 bp of intron 1 of a mouse April gene, ~202 bp of intron 1 of a human APRIL gene, exons 2 to 6 of a human APRIL gene, ~126 bp of human sequence 3' of exon 6 of a human APRIL gene, a self-deleting neomycin cassette flanked by LoxP recombinase recognition sites, mouse genomic sequence including the 3' UTR of a mouse April gene including ~83 bp 3' of the stop codon that appear in a mouse April gene, mouse genomic sequence including ~350 bp downstream of a mouse April gene and upstream of a mouse Senp3 gene, and a mouse Senp3 gene.

The final targeting vector was used to electroporate BALB-Rag2$^{-/-}$IL2Rγc$^{-/-}$ (DKO) mouse embryonic stem (ES) cells to create modified ES cells comprising an April gene at an endogenous April locus that is humanized from approximately the middle of intron 1 of a mouse April gene (~100 bp 3' of splice donor site) to approximately 100 bp 3' of the polyadenylation site of a human APRIL gene that was inserted into approximately the middle of the 3' UTR of a mouse April gene (FIG. 2B). Positively targeted ES cells containing a humanized April gene were identified by an assay (Valenzuela et al., supra) that detected the presence of the human APRIL gene sequence and confirmed loss of mouse April sequences. Table 4 sets forth the primers and probes that were used to confirm humanization of an endogenous April gene as described above. hAPRIL: human APRIL; mApril: mouse April.

Positive ES cell clones were then used to implant female mice using the VELOCIMOUSE® method (see, e.g., U.S. Pat. No. 7,294,754 and Poueymirou et al., F0 generation mice that are essentially fully derived from the donor gene-targeted ES cells allowing immediate phenotypic analyses, 2007, Nature Biotech. 25(1):91-99) to generate a litter of pups containing an insertion of exons 2 to 6 of a human APRIL gene into an endogenous April gene of a mouse. Mice bearing the humanization of exons 2 to 6 of an endogenous April gene were again confirmed identified by genotyping of DNA isolated from tail snips using a modification of allele assay (Valenzuela et al., supra) that detected the presence of the human APRIL gene sequences. Pups are genotyped and cohorts of animals heterozygous for the humanized April gene construct are selected for characterization.

Alternatively, humanization of an extracellular region of a April gene may be performed by direct modification of BAC clones by homologous recombination without de novo DNA synthesis as described above. For this method, a human APRIL gene that appears in human BAC clone CTD-2126o8 may be employed for humanizing an endogenous April gene of a mouse.

Briefly, a human BAC clone CTD-2126o8 (Invitrogen) was modified to delete a 3' region of the human APRIL gene which included a human SENP3 gene that started at approximately 350 bp 3' of the human APRIL gene. The modification is performed by homologous recombination in bacterial cells using a linearized targeting vector (e.g., pFHa0019) containing a self-deleting neomycin cassette flanked by recombinase recognition sites (e.g., LoxP; see U.S. Pat. Nos. 8,354,389 and 8,518,392, both of which are herein incorporated by reference) and a unique AsiSI restriction site positioned at the 3' of the cassette. The 5' homology arm of the targeting vector includes genomic sequence that is located between the human APRIL and SENP3 genes of the human BAC clone. The 3' homology arm of the targeting vector includes sequence of the BAC vector backbone. The modified human BAC clone that results from homologous recombination with the targeting vector is set forth in FIG. 3A. Chloramphenicol/neomycin double resistant bacterial colonies are selected and grown for preparation of modified BAC DNA containing a deletion of a human SENP3 gene. Correctly modified BAC clones are confirmed by PCR and sequencing.

Figure 3A:
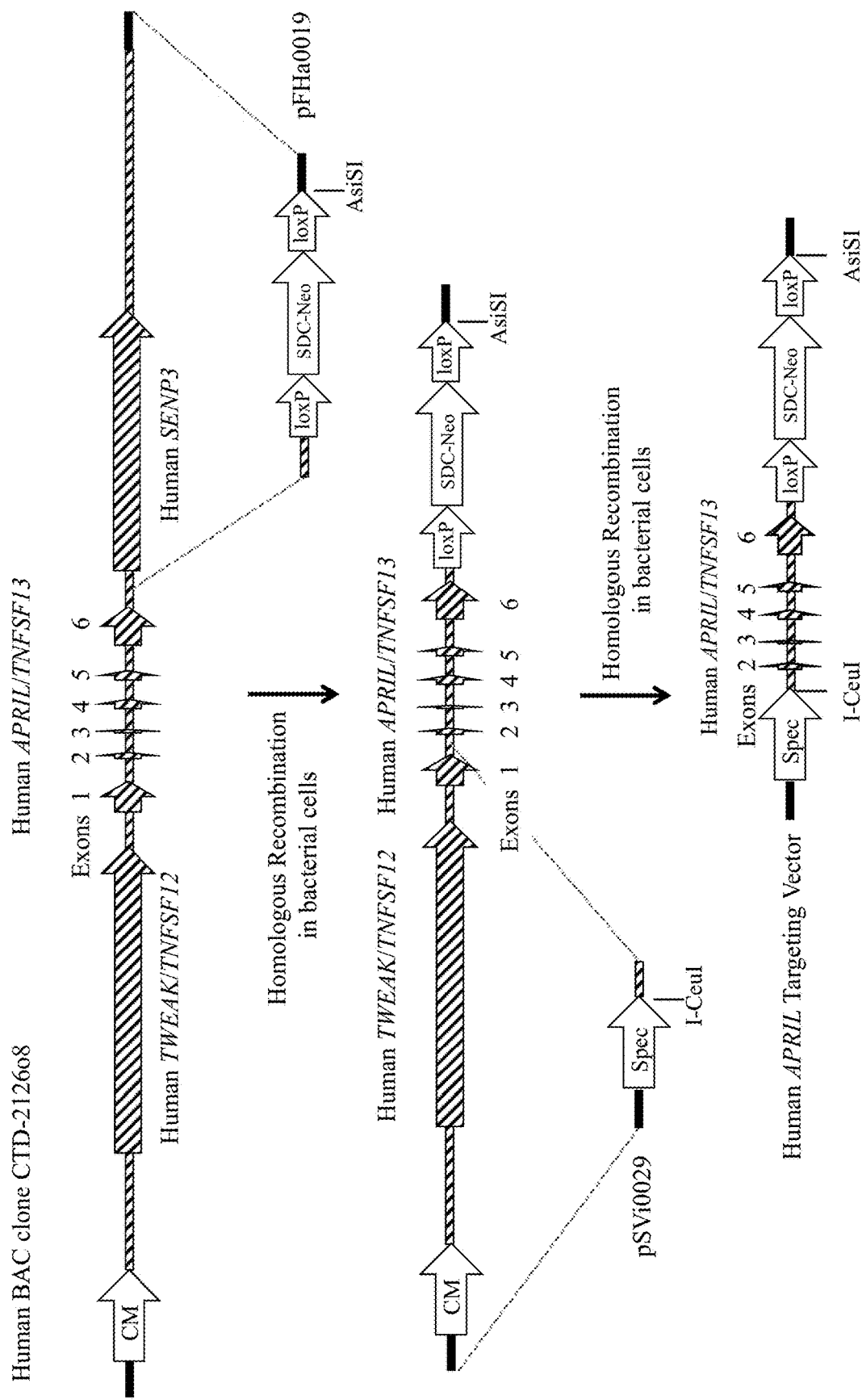
FIGS. 3A and 3B show diagrams, not to scale, of an alternative exemplary method for making a targeting vector for humanization of a non-human A PRoliferation-Inducing Ligand (April) gene. Non-human sequences are shown as closed, black symbols. Human sequences are shown in open, diagonal filled symbols. SDC Neo: self-deleting neomycin selection cassette. LoxP: Cre recombinase target recognition site sequence. CM: chloramphenicol selection cassette. Spec: spectinomycin selection cassette. Hyg: hygromycin selection cassette. Frt: Flp recombinase target recognition site sequence. Restriction enzyme recognition sites are indicated (e.g., AsiSI, MluI, HindIII, I-CeuI, etc.).

In a similar manner, the modified human CTD-2126o8 BAC clone (described above) is modified in a second step to delete a 5' human TWEAK gene contained in the human BAC clone. The targeting vector is constructed to include a 5' homology arm containing BAC vector sequence upstream of a selectable marker in the BAC vector backbone (e.g., chloramphenicol). This allows for easy screening of the resulting double targeted BAC clones by loss of resistance provided by the selectable marker from the BAC vector backbone (e.g., chloramphenicol) and gain of resistance from the different selectable marker in the targeting vector. An exemplary selection marker employed here is spectinomycin. The targeting vector is engineered with a 3' homology arm containing a unique restriction site (e.g., I-CeuI) and human genomic DNA sequence corresponding to intron 1 of a human APRIL gene. A targeting vector, depicted as pSVi0029 in FIG. 3A, is employed in homologous recombination in bacterial cells to create a double targeted human BAC clone containing deletions of a human TWEAK gene, exon 1 of a human APRIL gene, and a human SENP3 gene. The resulting bacterial cells containing the properly double targeted human BAC clone are spectinomycin/neomycin resistant. The final human APRIL targeting vector contains, from 5' to 3', a spectinomycin cassette, an I-CeuI site, ~202 bp of intron 1 of a human APRIL gene, exons 2 to 6 of a human APRIL gene, ~126 bp of human sequence 3' of exon 6 of a human APRIL gene, a self-deleting neomycin cassette flanked by LoxP recombinase recognition sites, and an AsiSI site.

Separately, a mouse BAC clone BMQ-223f24 (Invitrogen) is modified specifically to delete mouse genomic sequence containing exons 2 to 6 of a mouse April gene by homologous recombination in bacterial cells. An exemplary targeting vector may include a selection cassette that is different (e.g., hygromycin) from the selectable marker present in the BAC clone (e.g., chloramphenicol). The targeting vector containing, for example, a hygromycin cassette is engineered to append 5' and 3' homology arms containing mouse genomic sequence corresponding to mouse intron 1 and sequence including the 3' UTR of a mouse April gene including ~83 bp 3' of the stop codon that appear in a mouse April gene, respectively. The targeting vector is also engineered to contain unique restriction sites (e.g., I-CeuI and AsiSI) at 5' and 3' ends of the selection cassette. An exemplary targeting vector having the features described above, pNTu0002, is set forth in FIG. 3B. The linearized targeting vector is then used to replace the corresponding mouse sequence in BAC clone BMQ-223f24 by homologous recombination in bacterial cells. Positive clones containing a ~1776 bp deletion of mouse April exons 2 to 6 are selected using chloroamphenicol and hygromycin.

Figure 3B:
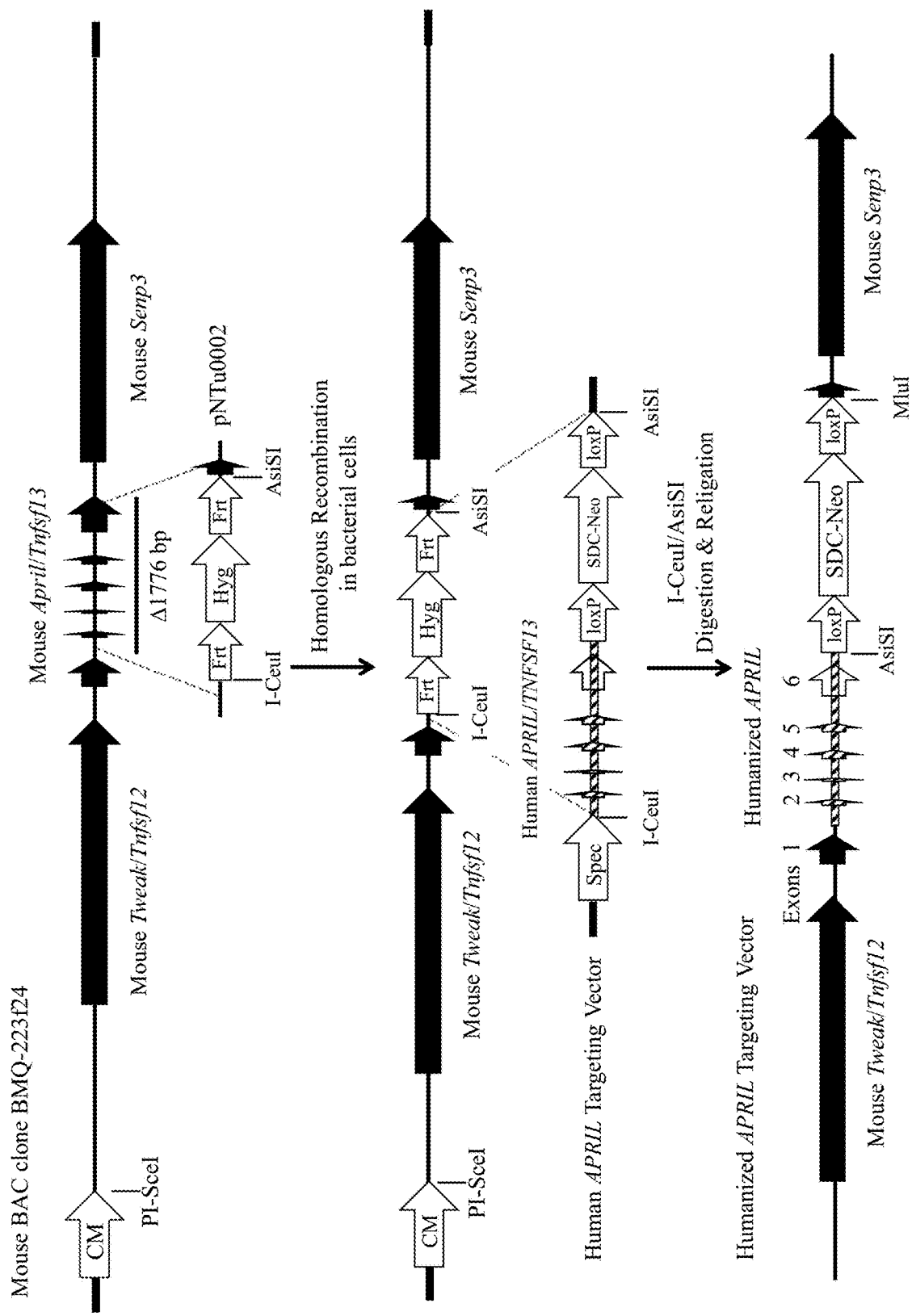

The human APRIL targeting vector and modified mouse BAC clone BMQ-223f24 containing a deletion of mouse April exons 2 to 6 are separately digested with I-CeuI and AsiSI to produce compatible cohesive fragments (FIG. 3B). The final targeting vector for humanizing a mouse April gene, made by ligation of the compatible restriction fragments, contains, from 5' to 3', contains, from 5' to 3', mouse genomic sequence including a mouse Tweak (Tnfsf12) gene and sequence 5' of a mouse April gene, a mouse April exon 1, ~100 bp of intron 1 of a mouse April gene, ~202 bp of intron 1 of a human APRIL gene, exons 2 to 6 of a human APRIL gene, ~126 bp of human sequence 3' of exon 6 of a human APRIL gene, a self-deleting neomycin cassette flanked by LoxP recombinase recognition sites, mouse genomic sequence including the 3' UTR of a mouse April gene including ~83 bp 3' of the stop codon that appear in a mouse April gene, mouse genomic sequence including ~350 bp downstream of a mouse April gene and upstream of a mouse Senp3 gene, and a mouse Senp3 gene.

The final humanized APRIL targeting vector is used to electroporate BALB-Rag2$^{-/-}$IL2Rγc$^{-/-}$ (DKO) mouse embryonic stem (ES) cells to create modified ES cells comprising an April gene that is humanized from approximately the middle of intron 1 of a mouse April gene (~100 bp 3' of splice donor site) to approximately 100 bp 3' of the polyadenylation site of a human APRIL gene that is inserted into approximately the middle of the 3' UTR of a mouse April gene (FIG. 3B). Positively targeted ES cells containing a humanized April gene are identified by an assay (Valenzuela et al., supra) that detects the presence of the human APRIL gene sequence and confirmed loss of mouse April gene sequences. Table 4 sets forth the primers and probes that are used to confirm humanization of an endogenous April gene as described above. hAPRIL: human APRIL, mApril: mouse April.

Positive ES cell clones may be used to implant female mice using the VELOCIMOUSE® method (see, e.g., U.S. Pat. No. 7,294,754 and Poueymirou et al., F0 generation mice that are essentially fully derived from the donor gene-targeted ES cells allowing immediate phenotypic analyses, 2007, Nature Biotech. 25(1):91-99) to generate a litter of pups containing an insertion of exons 2 to 6 of a human APRIL gene into an endogenous April gene of a mouse. Mice bearing the humanization of exons 2 to 6 of an endogenous April gene are identified by genotyping of DNA isolated from tail snips using a modification of allele assay (Valenzuela et al., supra) that detects the presence of the human APRIL gene sequences. Pups are genotyped and cohorts of animals heterozygous for the humanized April gene construct are selected for characterization.

TABLE 4

| Name | Location | Primer | Sequence (5'-3') | |
|---|---|---|---|---|
| mApril-1 | mApril exon 4 | Forward | GAGGCCCAGGGAGACATTG | SEQ ID NO: 13 |
| | | Reverse | GCAGGCTCAGGGCTTATCTG | SEQ ID NO: 14 |
| | | Probe | CGAGTCTGGGACACTGGAATTTATCTGC | SEQ ID NO: 15 |
| mApril-2 | mApril intron 5 | Forward | AACTTGCTCCATCCCTTACATC | SEQ ID NO: 16 |
| | | Reverse | GCTTGAGAGTTGGTTCCTTCCTTT | SEQ ID NO: 17 |
| | | Probe | TCACCTCCTGGGTTTGATTCCGA | SEQ ID NO: 18 |
| hAPRIL-1a | hAPRIL exon 3 | Forward | CCTGCACCTGGTTCCCATT | SEQ ID NO: 19 |
| | | Reverse | AGCCCGAGTTCCTGGTTATTGC | SEQ ID NO: 20 |
| | | Probe | AACGCCACCTCCAAGGGTGA | SEQ ID NO: 21 |
| hAPRIL-2a | hAPRIL exon 6, 3'UTR | Forward | AGGAGCCTCGGGTGTATCGTA | SEQ ID NO: 22 |
| | | Reverse | GCAGGGCTTGATCAGAAAGAAGAG | SEQ ID NO: 23 |
| | | Probe | CCCTGGTGTTGGTGTTGCCTCA | SEQ ID NO: 24 |

Example 2. Expression of Humanized A PRoliferation-Inducing Ligand (APRIL) in Non-Human Animals This example illustrates the characteristic expression of a humanized April gene in the cells of a non-human animal as described in Example 1. The humanized April gene encodes an April polypeptide that comprises the extracellular portion of a human APRIL protein linked to the intracellular portion of a non-human April protein. In this example, mRNA transcripts comprising exon 1 of a mouse April gene and exons 2 to 6 of a human APRIL gene were confirmed by reverse-transcriptase polymerase chain reaction (RT-PCR) using primers located in the human and mouse exon sequences of the humanized April gene.

Figure 4:
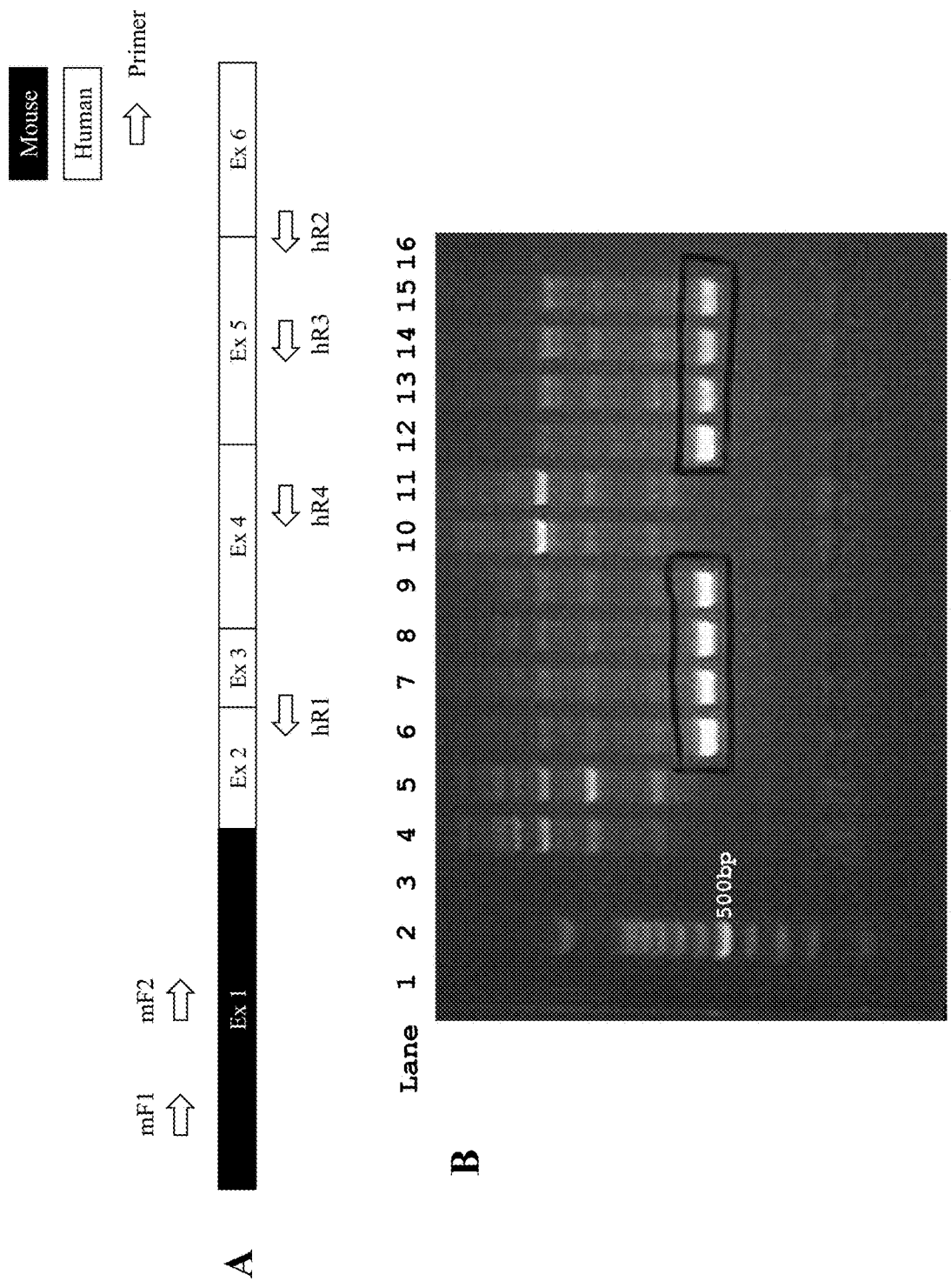
FIG. 4 shows (A) a schematic illustration, not to scale, of an mRNA transcript from a humanized April gene indicating human and mouse exons (e.g., Ex 1, Ex 2, etc.) and the locations of exemplary primers used to detect transcripts expressed from a humanized April gene, and (B) an exemplary electrophoresis gel showing PCR products amplified from mRNA isolated from bone marrow and splenocytes of wild-type mice (n=2) and mice heterozygous for a humanized April gene (n=4). From left to right: Lane 1: empty; Lane 2: 100 bp DNA ladder (New England Biolabs); Lane 3: empty; Lane 4: wild-type bone marrow; Lane 5: wild-type bone marrow; Lane 6: humanized Aprilbone marrow; Lane 7: humanized April bone marrow; Lane 8: humanized April bone marrow; Lane 9: humanized April bone marrow; Lane 10: wild-type splenocyte; Lane 11: wild-type splenocyte; Lane 12: humanized April splenocyte; Lane 13: humanized April splenocyte; Lane 14: humanized April splenocyte; Lane 15: humanized April splenocyte; Lane 16: empty. 500 bp: indicates the size of the more intense band for the molecular weight marker in Lane 2.

Briefly, cell suspension from bone marrow and spleens isolated from wild-type (WT) mice and mice heterozygous for a humanized April gene were made using standard methods. Bone marrow was collected from femurs by flushing with complete RPMI medium supplemented with fetal calf serum, sodium pyruvate, HEPES, 2-mercaptoethanol, non-essential amino acids, and gentamycin. Spleens were perfused with Collagenase D (Roche Bioscience) and erythrocytes from both spleen and bone marrow preparations were lysed with an ammonium chloride-based lysis buffer (e.g., ACK lysis buffer), followed by washing with complete RPMI medium. RNA was extracted from spleen and bone marrow preparations using TRIzol™ (Invitrogen) or Qiagen RNeasy™ Mini Kit (Qiagen) and primed with primers specific for mouse April exon 1 (mF1; AGTCAGAGAG CCAGCCCTT; SEQ ID NO: 25) and human APRIL exon 5 (hR3; ACATCGGAAT AGAGTCTCCT GC; SEQ ID NO: 26) using the Superscript™ III One-Step RT-PCR system (Invitrogen). Aliquots (5-10 µL) from each reaction were analyzed by agarose electrophoresis (FIG. 4). The predicted amplification product using the mF1 and hR3 primers was 526 bp. Reaction products were gel purified and confirmed by sequencing.

As shown in FIG. 4, expression of transcripts encoding an April polypeptide comprising the extracellular portion of a human APRIL protein linked to the intracellular portion of a non-human April protein was clearly detected in the spleen and bone marrow of heterozygous mice.

EQUIVALENTS

Having thus described several aspects of at least one embodiment of this invention, it is to be appreciated by those skilled in the art that various alterations, modifications, and improvements will readily occur to those skilled in the art. Such alterations, modifications, and improvements are intended to be part of this disclosure, and are intended to be within the spirit and scope of the invention. Accordingly, the foregoing description and drawing are by way of example only and the invention is described in detail by the claims that follow.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or the entire group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification.

Those skilled in the art will appreciate typical standards of deviation or error attributable to values obtained in assays or other processes described herein.

The publications, websites and other reference materials referenced herein to describe the background of the invention and to provide additional detail regarding its practice are hereby incorporated by reference.

What is claimed is:

1. A method of making a mouse, the method comprising the steps of:
   (a) replacing a mouse genomic fragment comprising exons 2-5 of an endogenous mouse April gene at an endogenous mouse April locus in a mouse embryonic stem (ES) cell with a genomic fragment comprising exons 2-6 of a human APRIL gene to form a humanized April gene at the endogenous mouse April locus, wherein the humanized April gene is under control of a mouse April promoter at the endogenous mouse April locus and encodes a humanized April protein comprising an extracellular portion of the human APRIL protein encoded by the human APRIL gene linked to an intracellular portion of the mouse April protein encoded by the mouse April gene; and wherein the coding exons of the humanized April gene consist of exon 1 of the endogenous mouse April gene and exons 2-6 of the human APRIL gene;
   (b) obtaining a modified mouse ES cell comprising the humanized April gene at the mouse endogenous April locus from (a); and,
   (c) creating a mouse using the modified mouse ES cell of (b), therein the mouse expresses the humanized April protein.

2. The method of claim 1, wherein the mouse does not detectably express a full-length endogenous mouse April protein.

3. The method of claim 1, wherein the humanized April protein comprises amino acid residues 87 to 250 of the human APRIL protein as set forth in SEQ ID NO: 5.

* * * * *